US012758736B2

(12) United States Patent
Wolf

(10) Patent No.: US 12,758,736 B2
(45) Date of Patent: Oct. 13, 2026

(54) VALVE ARRANGEMENT WITH SHUT-OFF UNIT AND PROCESS FOR OPERATING A VENTILATOR WITH SUCH A VALVE ARRANGEMENT

(71) Applicant: Drägerwerk AG & Co. KGaA, Lübeck (DE)

(72) Inventor: Andreas Wolf, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 1014 days.

(21) Appl. No.: 17/153,480

(22) Filed: Jan. 20, 2021

(65) Prior Publication Data

US 2021/0220604 A1 Jul. 22, 2021

(30) Foreign Application Priority Data

Jan. 21, 2020 (DE) ..................... 10 2020 000 335.4

(51) Int. Cl.
*A61M 16/20* (2006.01)
*A61M 16/00* (2006.01)

(52) U.S. Cl.
CPC ...... *A61M 16/209* (2014.02); *A61M 16/0003* (2014.02); *A61M 16/0051* (2013.01); *A61M 2016/0027* (2013.01)

(58) Field of Classification Search
CPC ............ A61M 16/209; A61M 16/0003; A61M 16/0051; A61M 2016/0027; A61M 39/22;
(Continued)

(56) References Cited

U.S. PATENT DOCUMENTS 4,059,657 A * 11/1977 Hay ...................... A61M 16/18
261/DIG. 65
4,316,458 A * 2/1982 Hammerton-Fraser ...................... A61M 16/20
128/205.24

(Continued)

FOREIGN PATENT DOCUMENTS

CN 2493226 Y 5/2002
CN 101121054 A 2/2008

(Continued)

OTHER PUBLICATIONS

Knight, "DE1960093A1," Jun. 9, 1971 (Year: 1971).*

*Primary Examiner* — Brandy S Lee
*Assistant Examiner* — Tina Zhang
(74) *Attorney, Agent, or Firm* — McGlew and Tuttle, P.C.

(57) ABSTRACT

A valve arrangement (1) for a fluid carrying system (18, 21). This fluid-carrying system (18, 21) is capable of establishing a fluid connection between a patient-side coupling unit (26, 27) and a ventilator (17). In an open position a shut-off unit (7) connects a patient-side port (3) to a device-side port (4) of the valve arrangement (1) and closes this fluid connection in a closed position. A locking unit is capable of locking the shut-off unit in both the open position and the closed position. When the shut-off unit is in the closed position and, in addition, a pressure above a preset pressure limit is present at the patient-side port, the shut-off unit is moved into the open position automatically and against a locking effect of the locking unit. A process for operating a ventilation system (2) with the ventilator and the valve arrangement is also provided.

20 Claims, 11 Drawing Sheets

(58) Field of Classification Search
CPC .... A61M 16/105; A61M 16/20; A61M 16/00; A61M 16/201; A61M 16/208; B33Y 10/00; B33Y 80/00; F16K 1/2007; F16K 17/025; F16K 17/0413; F16K 31/563; F16K 35/00; F16K 17/02; F16K 31/60; F16K 37/005; F16K 15/1821; F16K 31/06; F16K 15/1841; F16K 15/0493
See application file for complete search history.

(56) References Cited

U.S. PATENT DOCUMENTS

| | | | | |
|---|---|---|---|---|
| 4,572,176 | A * | 2/1986 | Walther | A62B 9/022 128/204.26 |
| 5,368,017 | A * | 11/1994 | Sorenson | A61M 16/0858 128/207.14 |
| 5,501,213 | A * | 3/1996 | Jackson | B63C 11/2227 128/205.24 |
| 6,899,312 | B2 | 5/2005 | Türker et al. | |
| 10,101,237 | B2 * | 10/2018 | Decker | G01M 3/007 |
| 2002/0069878 | A1 * | 6/2002 | Lurie | C09K 5/042 128/200.24 |
| 2007/0000671 | A1 * | 1/2007 | Reilly | A62C 35/68 169/17 |
| 2007/0181125 | A1 * | 8/2007 | Mulier | F16K 37/005 128/204.21 |
| 2008/0083467 | A1 * | 4/2008 | Taylor | F16K 17/406 137/624.27 |
| 2010/0094366 | A1 * | 4/2010 | McCarthy | A61M 16/12 128/204.23 |
| 2010/0269829 | A1 | 10/2010 | Hansmann et al. | |
| 2010/0282253 | A1 * | 11/2010 | Newman, Jr. | A61M 16/208 128/205.24 |
| 2011/0232640 | A1 * | 9/2011 | Van Dijk | A61M 16/20 128/205.24 |
| 2013/0317765 | A1 * | 11/2013 | Rao | A61M 16/026 702/51 |
| 2014/0058524 | A1 | 2/2014 | Gray | |
| 2014/0246024 | A1 * | 9/2014 | Cragg | A61M 16/0833 128/204.19 |
| 2015/0306329 | A1 | 10/2015 | Brown et al. | |
| 2016/0325066 | A1 * | 11/2016 | Fuller | A61M 16/209 |
| 2020/0129721 | A1 | 4/2020 | Tappehorn et al. | |
| 2020/0129726 | A1 | 4/2020 | Tappehorn et al. | |

FOREIGN PATENT DOCUMENTS

| | | | |
|---|---|---|---|
| CN | 203943996 | U | 11/2014 |
| CN | 104623798 | A | 5/2015 |
| CN | 106110455 | A | 11/2016 |
| DE | 1960093 | A1 | 6/1971 |
| DE | 3801444 | A1 | 7/1989 |
| DE | 69911704 | T2 | 4/2004 |
| DE | 10240992 | B4 | 1/2011 |
| DE | 202007019350 | U1 | 1/2012 |
| DE | 102018003026 | A1 | 10/2019 |
| DE | 102018008495 | A1 | 4/2020 |
| EP | 0978291 | A1 | 2/2000 |
| WO | 2008028228 | A1 | 3/2008 |
| WO | 2015014899 | A1 | 2/2015 |

* cited by examiner

VALVE ARRANGEMENT WITH SHUT-OFF UNIT AND PROCESS FOR OPERATING A VENTILATOR WITH SUCH A VALVE ARRANGEMENT

CROSS REFERENCE TO RELATED APPLICATIONS

This application claims the benefit of priority under 35 U.S.C. § 119 of German Application 10 2020 000 335.4, filed Jan. 21, 2020, the entire contents of which are incorporated herein by reference.

TECHNICAL FIELD

The present invention pertains to a valve arrangement, which is arranged in a fluid connection, e.g., in a ventilation circuit, between a ventilator and a patient or can be arranged there, wherein the ventilator ventilates the patient mechanically and wherein the valve arrangement opens automatically in a certain overpressure situation. The present invention pertains, furthermore, to a process for operating a ventilation system comprising a ventilator and a valve arrangement according to the present invention.

TECHNICAL BACKGROUND

Various valve arrangements for medical applications with pressure relief valves have become known.

An arrangement, which limits the pressure or the volume flow in a patient circuit, is described in US 2015/0 306 329 A1. The arrangement can be connected to an endotracheal catheter (endotracheal tube 113) and comprises a proximal end 110 with an adapter 109. There is a pressure relief valve (relief valve 205) in one adapter 409, 501, and there is a throttling valve (309) in an adapter 306. The throttling valve 309 can be adjusted by means of an actuating element (valve control surface 304, groove 305, stem 303) and it is capable as a result of adjusting the cross-sectional area of a flow opening (aperture 301). If the pressure in the patient circuit (more precisely, in the hollow main body 213) exceeds a limit, the pressure relief valve 205 opens against the force of a retaining mechanism 208.

DE 699 11 704 T2 shows a ventilator, which can be operated optionally in the "mechanical ventilation mode" or in the "breathing assist" mode. In the "mechanical ventilation" mode, breathing gas from the source 25 is sent via a connection 23 into a tube 4, which sends breathing gas to a patient. A line 12, which leads into the tube 4, is blocked. The line 12 is opened and the connection 23 is blocked in the "breathing assist" mode. The feed of breathing gas into the line 12 is controlled by means of the valve 29. A limiter 30 limits the volume flow and/or the pressure of the breathing gas being fed.

A pressure relief valve 1 for ventilators is described in DE 102 40 992 B4. A movable valve disk 6 lies on a valve seat of a breathing gas line. When the pressure relief valve 1 is being operated in the "manual ventilation" mode, an overpressure is capable of opening the pressure relief valve 1 against a preset closing force. The preset closing force of the valve disk 6 can be changed by means of a handwheel 2.

DE 20 2007 019 350 U1 and WO 2008/028228 A1 show a valve arrangement, which lowers the exhalation pressure while a patient is using a breathing mask during a CPAP therapy and is being ventilated mechanically. This ventilation system is arranged at a pipeline, which connects the breathing mask to a flow generator. In one embodiment, the ventilation system comprises a demand valve, which opens when the patient is inhaling or breathing air is being delivered to the patient, and it closes when the patient is exhaling. A pressure relief valve at the mask opens in case of an overpressure at the mask. In one embodiment, the demand valve has a flap, which is locked in both the opened position and in the closed position. The locking is released in the closed position of the flap and the flap opens when the exhalation pressure drops below a preset limit.

A ventilation tube device 10, which connects a patient to a ventilation system 110, is described in the post-published unexamined German patent application DE 10 2018 008 495 A1. A pressure limiting element 30 is arranged in the ventilation tube device 10. This pressure limiting element 30 can move to and fro between a flow position 31 and a blocked position 32.

SUMMARY

A basic object of the present invention is to provide a valve arrangement for a ventilator as well as a process for operating a ventilation system comprising a ventilator and a valve arrangement, wherein the valve arrangement and the process offer a higher level of operational reliability than do prior-art valve arrangements in different situations.

The valve arrangement according to the present invention is configured to be used in a fluid carrying system, especially in a system with flexible tubes and/or tubes. This fluid carrying system is capable of establishing a fluid connection between a patient-side coupling unit and a ventilator, wherein fluid can flow in both directions through the fluid connection.

An anesthesia device is a special case of a ventilator in the sense of this disclosure. A fluid carrying unit is capable of carrying fluid between two points and of preventing an escape of the fluid between the two points to the extent possible, without necessarily moving the fluid itself. The patient-side coupling unit can be connected to the patient, so that a fluid connection can be established between the ventilator and the patient when the patient is connected to the patient-side coupling unit.

The valve arrangement according to the present invention comprises a patient-side port and a device-side port. A fluid connection can be established between the device-side port of the valve arrangement and a ventilator by means of a suitable fluid carrying unit. A fluid connection can be established between the patient-side port of the valve arrangement and a patient-side coupling unit by means of an additional, suitable fluid carrying unit for a patient, who shall be mechanically ventilated by the ventilator. The valve arrangement according to the present invention may also be arranged in a single fluid carrying unit between the patient-side coupling unit and the ventilator, in which case the two ports of the valve arrangement are integrated into this fluid carrying unit.

A shut-off unit of the valve arrangement according to the present invention can move to and fro between at least one open position and a closed position and optionally between each of the plurality of possible open positions and the closed position. If the shut-off unit is in the open position or in an open position, a fluid communication is established or can be established between the two ports of the valve arrangement. This fluid communication is interrupted or is—compared to the open position or to each open position—at least limited, i.e., the flow rate of fluid is reduced when the shut-off unit is in the closed position.

The locking unit can be moved into an open locked state and into a closed locked state. In the open locked state, the locking unit locks the shut-off unit in the open position or in an open position. In the closed locked state, the locking unit locks the shut-off unit in the closed position. Consequently, a locking effect of the locking unit, for example, a counter-acting locking force, must be overcome in order to move the locking unit from one position into the other position or into another position. Or else, a locking body of the locking unit must be moved from a locked position into a released position, in which the locking body does not lock the shut-off unit any longer.

When the shut-off unit is in the closed position and when, in addition, a pressure above a preset pressure limit is present at the patient-side port, the valve arrangement moves the shut-off unit automatically into the open position or into an open position, doing so against a locking effect of the locking unit. In particular, the valve arrangement further comprises a pressure responsive means configured to automatically move, with the locking unit in the closed position, the shut-off unit against the locking effect of the locking unit into the at least one open position with a pressure above a preset pressure limit present at the patient-side port.

The present invention pertains, furthermore, to a process for operating a ventilation system. The ventilation system comprises a ventilator, which is capable of ventilating a patient, as well as at least one valve arrangement according to the present invention. The patient is connected to a patient-side coupling unit. The ventilator may be configured as an anesthesia device. A fluid connection is established between the ventilator and the device-side port of the valve arrangement or of a valve arrangement at least from time to time. An additional fluid connection is established between the patient-side coupling unit and the patient-side port of this valve arrangement at least from time to time.

The process comprises the following steps:

- The ventilator ventilates the patient mechanically at least from time to time. The two established fluid connections are used for the mechanical ventilation.
- The shut-off unit is in the open position or in an open position during the mechanical ventilation. A fluid stream flows through the valve arrangement. The fluid stream flows at least from the ventilator to the patient-side coupling unit. The fluid stream optionally flows alternatingly from the ventilator to the patient-side coupling unit or conversely, from the patient-side coupling unit to the ventilator, while the shut-off unit is in the open position.
- The locking unit locks the shut-off unit in the open position during the mechanical ventilation.
- The mechanical ventilation is subsequently ended or at least interrupted.
- The shut-off unit is moved into the closed position.
- The locking unit locks the shut-off unit in the closed position.
- Then, when the shut-off unit is in the closed position and, in addition, a pressure above a preset pressure limit is present at the patient-side port, the valve arrangement moves the shut-off unit automatically and against a locking effect of the locking unit into the open position or into an open position.

It will be described below what possible advantages of the present invention may arise in many situations.

The shut-off unit can be moved according to the present invention to and fro between at least one open position and a closed position. The shut-off unit makes it possible in the open position or in an open position for a fluid to flow through the valve arrangement and a fluid connection is established or can be established between the patient-side coupling unit and the ventilator. In the closed position, the shut-off unit interrupts this fluid connection or it at least reduces the flow rate through the fluid carrying system compared to each open position. The shut-off unit consequently makes possible a mechanical ventilation in the open position or in at least one open position. In the closed position, the shut-off unit preferably separates a patient-side coupling unit from the ventilator and from the environment.

It is necessary in many cases from time to time to sever the fluid connection between a patient-side coupling unit and the ventilator, for example, because the patient shall be transported, the ventilator or the fluid carrying system must be cleaned or maintenance has to be performed on it, or because operating materials must be added or replaced. The patient-side coupling unit, e.g., a ventilation tube or a catheter or a face mask, is connected to the patient and shall be connected, as a rule, to the patient also after the separation from the ventilator. However, the fluid connection also has to be severed when the patient is transported from a first ventilator to a second ventilator, for example, because the first ventilator is a transportation ventilator, which ventilates the patient onboard an ambulance vehicle and/or on a stretcher, which is transporting the patient being ventilated mechanically to a hospital and the second ventilator will then ventilate the patient in the hospital. The patient shall be connected to the patient-side coupling unit in this case as well.

When the shut-off unit is in the closed position, the fluid connection between the patient and the ventilator can be severed without a fluid connection being established thereby between the patient and the environment. Such a fluid connection of the patient to the environment is undesired in many cases, especially because a residual air pressure (positive end-expiratory pressure, PEEP) in the lungs of the patient may then become too low and the lungs can collapse. It often takes hours to then bring the lungs again into a state in which they are able to function. The “inflation” of the lungs inevitably exerts shearing forces on the alveoli (air sacs), which leads to their being worn. In the closed locked state, the locking unit reduces the risk that the shut-off unit will open and the fluid connection will be established thereby unintentionally.

Thanks to the shut-off unit, it is not necessary to sever the fluid connection manually and then to close it, for example, by somebody pulling off a flexible tube and inserting a plug. The shut-off unit can be configured such that the shut-off unit interrupts the fluid connection in the closed position essentially completely, at least for the time period during which the patient is not being ventilated mechanically. This time period is, as a rule, only a few minutes. The step of moving the shut-off unit into the closed position often requires less time than other possible procedures for interrupting the fluid connection between the patient and the ventilator, and it reduces the risk of establishment of an undesired fluid connection between the lungs and the environment.

According to the present invention, the locking unit locks the shut-off unit, doing so both in the open position or in each possible open position or at least in one of several possible open positions as well as in the closed position. The locking unit consequently provides for a bistable locking for the shut-off unit. This bistable locking reduces the risk of an unintended opening or closing of the shut-off unit, which can happen without a suitable locking, for example, because of vibrations, shocks or contacts or incorrect actions of a user.

As was just described, an undesired fluid connection may become established between the lungs of the patient and the environment in case of an unintentional opening. It could happen in case of an unintentional closure that the patient would not be supplied with a sufficient amount of air. Since the shut-off unit is only opened at a pressure above the pressure limit, the locking unit prevents the shut-off unit from opening unintentionally when the patient exhales only slightly or is coughing and the pressure at the patient-side port remains below the pressure limit.

In addition, the valve arrangement may be configured such that the locked shut-off unit remains in the closed position, regardless of how high the pressure is at the device-side port, and it will not open by itself but only after an unlocking. This configuration reduces the risk of the shut-off unit opening unintentionally. If the fluid connection is interrupted and the shut-off unit is opened, the lungs of the patient could as a result be in a fluid connection with the environment, which is, as was described above, undesirable. With the fluid connection established and with the shut-off unit being opened unintentionally, the patient could be exposed to a high pressure from the device-side port or to a fluid not intended for the mechanical ventilation. The valve arrangement can be configured such that the shut-off unit opens automatically only at a high pressure at the patient-side port and is otherwise locked and can be unlocked and then moved only after a manual intervention. This configuration increases the operational reliability both when a fluid connection is established to a ventilator and when such a fluid connection is absent.

In addition, a relatively simple mechanical construction of the valve arrangement is possible in many cases. The valve arrangement according to the present invention causes the fluid connection to be opened or closed in the desired and operationally reliable manner, and the valve arrangement provides at the same time an automatically acting pressure relief mechanism.

According to the present invention, the valve arrangement is capable of moving the shut-off unit automatically from the closed position into the open position or into an open position, doing so against a locking effect of the locking unit, doing so specifically when a pressure above the pressure limit is present at the patient-side port. This feature reduces the risk of the patient's health being compromised, especially in the following situation: The patient is connected to a patient-side coupling unit, and the fluid connection to the ventilator is established or is temporarily interrupted. The shut-off unit is in the closed position, and the lungs of the patient are not in a fluid connection with the ventilator as a consequence, and they are not in a fluid connection with the environment, either. It is possible that the patient coughs in this situation and exhales forcefully in another manner. If the shut-off unit should remain in the closed position in this situation, a high pressure and/or a high and/or rapid pressure rise would occur on the patient side, doing so often abruptly. The resulting high pressure/pressure increase cannot disappear rapidly enough with the shut-off unit closed and it affects the lungs. This effect can lead to damage to the lungs, for example, to a barotrauma. The shut-off unit is opened automatically according to the present invention in this situation, and the pressure, which develops because of the coughing or forceful exhalation, can escape through the valve arrangement into the environment. The risk of development of the lung damage just described is therefore markedly reduced.

The valve arrangement responds automatically and moves the shut-off unit into the open position when a pressure above the pressure limit is present at the patient-side port. It is possible, but not necessary thanks to the present invention for the patient themselves, or any other person, to open the shut-off unit manually, e.g., while the patient is coughing. The risk of damage to the lungs is also reduced when the patient cannot open the shut-off unit, for example, because the patient is partially sedated, and the coughing is not noticed by any other person.

According to the present invention, the valve arrangement opens the shut-off unit when a pressure above the pressure limit is present at the patient-side port. This pressure limit can be set by a construction of the valve arrangement. The pressure limit can be preset, for example, by a corresponding configuration of the locking unit such that, on the one hand, the pressure limit is below the pressure that is present when the patient is coughing with a sufficient force or is exhaling with a sufficient force otherwise and thereby generates a pressure above the pressure limit with the shut-off unit closed. With the shut-off unit closed, the risk of damage to the lungs would be present. The valve arrangement responds automatically and moves the shut-off unit automatically, i.e., without the patient having to monitor themself or without another person having to monitor the patient and having to move the shut-off unit when needed. The risk of damage to the patient's lungs due to a high pressure/pressure increase after an intense coughing is reduced. On the other hand, the pressure limit is high enough for the shut-off unit to remain locked in the closed position for an unintended opening being therefore prevented in case of shocks, vibrations, contacts, unintended incorrect actions or in case of an only mild cough or exhalation of the patient. Since the shut-off unit remains in the closed position below the pressure limit, the risk of the residual pressure (PEEP) in the lungs becoming too low because of vibrations or a mild cough is reduced.

The triggering event, namely, a pressure above the pressure limit at the patient-side port, can be used in many cases directly in a simple manner to move the shut-off unit automatically, especially by means of a simple mechanical configuration. It is possible but not necessary thanks to the present invention automatically to detect coughing of the patient, e.g., by a corresponding pneumatic or electrical or optical or acoustic sensor. The unintended high pressure increase occurring during coughing is prevented thanks to the valve arrangement according to the present invention, and this happens especially automatically and without a person having to respond quickly.

The present invention makes it possible that, even though the pressure at the patient-side port above the pressure limit is the triggering event for the shut-off unit being moved against the locking effect into the open position, it is possible, albeit not necessary for the pressure present at the patient-side port to overcome alone the locking effect of the locking unit. This pressure is generated in many cases solely by a spontaneously breathing patient and it is therefore limited. It is possible that an additional mechanism of the valve arrangement according to the present invention overcomes the locking effect. As a result, the locking unit can exert a stronger locking force (higher pressure limit), which increases the operational reliability, and a spontaneously breathing patient can nevertheless cause the shut-off unit to be opened automatically, for example, by a cough.

According to the present invention, the shut-off unit is locked in both positions. In addition, the valve arrangement overcomes the locking effect of the locking unit when the shut-off unit is in the closed position and the pressure present at the patient-side port is above the pressure limit. These features do, in particular, distinguish the valve arrangement according to the present invention from a device with a usual pressure relief valve, which typically opens in case of overpressure against a restoring force and closes again at a lower pressure. A pressure relief valve may also respond unintentionally, e.g., in case of vibrations or shocks or contact, and it is not locked in any position. Moreover, the valve arrangement according to the present invention may be configured such that even though it opens the shut-off unit automatically at a sufficiently high pressure at the patient-side port, it does not otherwise move the shut-off unit automatically, regardless of how high the pressure is at the device-side port. A conventional pressure relief valve at a fluid connection opens, as a rule, at a sufficiently high pressure, regardless of which side this pressure is present on.

The present invention avoids the need to provide a conventional pressure relief valve in order to reduce the risk of damage to the lungs. Since the valve arrangement according to the present invention provides a mechanism that offers protection against an undesired overpressure, there is no need for a pressure relief valve that is separated in space from the shut-off unit, which saves installation space and leads to a weight reduction. In particular, it is not necessary to arrange a pressure relief valve at the patient-side coupling unit. The present invention may also be used combined with a conventional pressure relief valve.

According to the present invention, the valve arrangement opens the shut-off unit against the locking force when a pressure above the pressure limit is present at the patient-side port. This feature does, in particular, distinguish the valve arrangement according to the present invention from an arrangement known, e.g., from DE 20 2007 019 350 U1, which can be used during a mechanical ventilation and in which the shut-off unit opens when air flows to the patient-side coupling unit and closes when air flows away from the patient-side coupling unit. The shut-off unit described in DE 20 2007 019 350 U1 opens at a low pressure at the patient-side port, it closes again at a higher pressure and can be used during a mechanical ventilation, but not when the fluid connection between the patient-side coupling unit and the ventilator is interrupted and an undesired fluid connection between the lungs of the patient and the environment shall be prevented. By contrast, the valve arrangement according to the present invention opens the shut-off unit at a sufficiently high pressure at the patient-side port and can therefore be used both when the fluid connection between the patient-side coupling unit and the ventilator is established as well as when it is interrupted or ended.

The valve arrangement preferably comprises a fluid carrying unit, which connects the two ports to one another in a fluid-carrying manner and which is preferably integrated in the fluid carrying system between the patient-side coupling unit and the ventilator. In the closed position, the shut-off unit closes this fluid carrying unit completely or at least partially. This configuration makes it possible to arrange the two ports of the valve arrangement separated from one another in space and separated from the shut-off unit. It is made possible to adapt the two ports independently from one another to a respective applicable standard.

According to the present invention, the shut-off unit is automatically moved (transferred) from the closed position into the open position or into an open position when a pressure above the pressure limit is present at the patient-side port. In a preferred embodiment, this event automatically causes the locking unit to lock the shut-off unit being moved in this open position. The shut-off unit is prevented thereby from being closed again unintentionally after the opening, which may happen in case of a usual restoring element or of a usual pressure relief valve. The shut-off unit, which is closed again, could lead to a high pressure acting on the lungs of the patient. If the shut-off unit were not locked in the open position or in an open position, it could again reach the closed position and then prevent the patient in their attempt to inhale again after coughing. Furthermore, the locking prevents a patient, who is coughing over a longer time, from bringing about an oscillation of the shut-off unit between two positions, which is likewise often undesired, especially because of the mechanical wear and/or a possible noise generation.

The shut-off unit preferably remains in the closed position even at a pressure above the pressure limit, which pressure is present at the device-side port. This leads to a reduction of the risk that an excessively high pressure will act on the patient, especially with the fluid connection established.

The shut-off unit preferably comprises a mechanical or pneumatic spring and/or a locking body. The shut-off unit is configured especially by means of this configuration such that it operates largely independently from the direction of the force of gravity relative to the valve arrangement. This effect is especially advantageous because the valve arrangement may be arranged in nearly any position relative to the patient, relative to the ventilator and relative to the force of gravity, and the shut-off unit may be located in the open position especially above, under or next to a fluid connection between the patient and the ventilator. If the orientation of the valve arrangement according to the present invention changes in the course of a use, this does not substantially affect the locking effect.

In one embodiment, the pressure, which is present at the patient-side port and is generated, as a rule, by the patient, moves the shut-off unit directly against the locking effect into the open position or into an open position, for example, by means of a nonreturn valve, which moves under the pressure present and moves the shut-off unit into the open position, when the pressure present is above the pressure limit. At a pressure that is equal to or higher than the pressure limit, the locking effect is consequently overcome or abolished.

By contrast, the following configuration of the shut-off unit is possible as well: The locking unit locks the shut-off unit in the closed locked position even when the pressure present at the patient-side port is higher than or equal to the pressure limit, but it is below a higher additional pressure limit, or also at any pressure present at the patient-side port. The locking effect is in many cases high and reliable enough to prevent an unintended opening of the shut-off unit. In a preferred embodiment, the valve arrangement comprises a pressure relief mechanism. This pressure relief mechanism responds when the shut-off unit is in the closed position and the pressure present at the patient-side port is then above the pressure limit, and it moves in this situation the shut-off unit against the locking effect into the open position. The pressure relief mechanism avoids a possible drawback, which could develop when the pressure generated by the patient would have to move the shut-off unit directly against the locking effect. In case of such a direct coupling without a pressure relief mechanism, either would the patient be at a risk during intense coughing because the pressure limit is too high, or the locking unit would not exert a sufficient locking effect because the pressure limit would be too low.

In the closed locked state, the locking unit holds the shut-off unit in the closed position. The optional pressure relief mechanism preferably responds automatically when the pressure at the patient-side port is above the pressure limit in this situation. The pressure relief mechanism overcomes the locking effect of the locking unit. Thanks to the pressure relief mechanism, the pressure limit may be selected, on the one hand, to be so low that coughing or another violent exhalation of the patient triggers the pressure relief mechanism and the latter will automatically open the shut-off unit. On the other hand, the pressure limit may be so high and, in particular, the locking unit may be configured such that the locking effect will also hold the shut-off unit in the closed position even in case of usual vibrations and shocks. The pressure relief mechanism practically increases the force that originates from the pressure present at the patient-side port. In one embodiment, the pressure present at the patient-side port activates the pressure relief mechanism.

The pressure relief mechanism does not preferably influence the shut-off unit as long as the pressure at the patient-side port is below the pressure limit or the shut-off unit is in the open position. In particular, the pressure relief mechanism does not depend on how high the pressure is at the device-side port. If the shut-off unit is in the closed position, it would in many cases be undesirable for a sufficiently high pressure acting on the device-side port to open the shut-off unit and for this pressure then to act on the patient. In addition, the pressure relief mechanism does not preferably influence the shut-off unit when this is in the open position. Therefore, the pressure relief mechanism does not compromise/interfere with the process of the ventilator mechanically ventilating the patient.

In one embodiment, the pressure relief mechanism comprises at least one spring, which is preferably pretensioned by a movement of the shut-off unit into the closed position and is held in the pretensioned state. At a pressure above the pressure limit at the patient-side port, locking or another kind of blocking of the pretensioned spring is automatically abolished, and the relaxing spring moves the shut-off unit against the locking effect into the open position or into an open position. This configuration leads to a simple and preferably purely mechanical pressure relief mechanism. This spring may be a compression spring or a tension spring and operate mechanically or even pneumatically. A plurality of springs arranged in parallel are possible.

In one embodiment, the shut-off unit can be moved only against the locking effect of the locking unit. In another embodiment, the locking unit can be moved from at least one locked state, preferably from each locked state, into an optional released state, and it exerts no or at least only a weaker locking effect in the released state compared to the two locked states. It is possible that the locked shut-off unit can be moved with a stronger force only, so that there is a risk that the fluid connection is unintentionally interrupted on the basis of this movement. To move the shut-off unit, the locking unit must first be moved into the released state in this embodiment.

The shut-off unit can preferably be brought by means of an actuating unit from the open position or from at least one open position into the closed position and back again from the closed position into the open position, i.e., the shut-off unit can be actuated manually. The actuating unit may be arranged directly at the valve arrangement or be located at a spaced location in space from the valve arrangement and be in a connection with an adjusting member for the shut-off unit, for example, by means of radio waves. This feature makes it possible to sever a fluid connection rapidly by the valve arrangement and to restore it again. It is not necessary to separate a patient-side fluid carrying unit from a ventilator and to close it after the separation with a special cap or even manually in order to prevent an undesired fluid connection between the patient and the environment. A closure made in this manner is frequently unhygienic and/or it does not interrupt the undesired fluid connection in a reliable manner and/or sufficiently and/or rapidly enough.

It is possible that the valve arrangement moves the shut-off unit into the open position automatically at a pressure above the pressure limit and it additionally moves the locking unit into the optional released state. The shut-off unit is not locked any more after that. It is also possible that the shut-off unit is automatically moved again into the closed position after the end of a preset time period.

In a preferred embodiment, the valve arrangement causes, by contrast, the shut-off unit to be moved into the open position or into an open position and, in addition, the locking unit to be moved into the open locked state when the pressure at the patient-side port is above the pressure limit. In one embodiment, the optional pressure relief mechanism is capable of carrying out this additional step. The valve arrangement, i.e., the pressure present at the patient-side port and/or optionally the pressure relief mechanism, consequently causes additionally the shut-off unit to be locked in the open position. The shut-off unit is prevented thereby from closing again accidentally or unintentionally, for example, because of vibrations or shocks or contacts. Actuation of the actuating unit is necessary to bring the shut-off unit into the closed position again.

In one embodiment, the valve arrangement comprises a safety element, which can be actuated manually, e.g., a button or a movable disk. When the safety element is in an inoperative position, it holds the locking unit in the open locked state. The safety element preferably holds the locking unit in the closed locked state in the same inoperative position or in another inoperative position. After a user actuates the safety element and has moved it out of the inoperative state thereby, the locking unit is moved into the optional released state and it does not lock the shut-off unit any longer, but it releases same. The safety element consequently reduces the risk of an unintended unlocking of the shut-off unit and of being moved as a consequence unintentionally.

This configuration can be combined with the above-described actuating unit and it avoids the need to have to move the actuating unit against the locking effect of the locking unit. The locking unit can exert a stronger locking force in a locked state compared to a configuration without a released state and without a safety element, which further reduces the risk of an unintended movement of the shut-off unit. On the other hand, a weaker force is necessary to open or to close the shut-off unit manually when the safety element is in the released state compared to an embodiment without safety element. A restoring element preferably holds the safety element in the inoperative position and it seeks to move the safety element out of the released position again into the inoperative position.

In one embodiment, the valve arrangement additionally comprises a pressure relief valve. If a pressure above an overpressure limit is present at the device-side port, this pressure relief valve opens, preferably against the force of a restoring element. This pressure relief valve is preferably located between the shut-off unit when this is in the closed position and the device-side end of the valve arrangement, e.g., in the device-side port. This pressure relief valve opens especially when the ventilator is carrying out ventilation strokes with the shut-off unit closed. The shut-off unit is prevented from being opened unintentionally and the patient is prevented from being put at risk. Furthermore, the risk of damage to the ventilator or to the fluid carrying system is reduced.

According to the present invention, the shut-off unit is moved against the locking effect of the locking unit from the closed position into the open position or into an open position when a pressure above the pressure limit is present at the patient-side port. This pressure limit is preset as a fixed value by the construction of the valve arrangement in one embodiment.

In another embodiment, the valve arrangement additionally comprises an adjusting unit for changing the pressure limit. A user can change the pressure limit manually by means of this optional adjusting unit and adjust thereby especially the valve arrangement to a patient. This adjusting unit is capable, for example, of changing the locking effect of the locking unit or even an activating element of the above-described optional pressure relief mechanism. For example, the locking unit comprises a mechanical or pneumatic spring, which exerts a locking effect, or holds a locking body of the locking unit in a locked position. The mechanical tension or a pneumatic property of this spring can be changed by means of the adjusting unit.

It is possible that the optional adjusting unit makes possible a continuous change of the pressure limit within a preset range. In a preferred embodiment, the adjusting unit snaps in when the pressure limit is set at one of several possible values, and it can be moved further by exerting a certain force only. This preferred embodiment prevents the pressure limit from being unintentionally set at an excessively high value or at an excessively low value, which could happen without a snapping in when the adjusting unit is moved unintentionally or is actuated in another way unintentionally.

In one embodiment, the locking unit is capable of locking the locking unit in exactly one closed position and in exactly one open position. These two positions are preferably the two possible end positions of the locking unit and especially preferably also the two end positions of the actuating unit. In another configuration, the locking unit is capable of additionally locking the shut-off unit in at least one intermediate position between the closed position and the open position. A fluid communication between the two ports is possible in this intermediate position as well, but it is possible at a lower flow rate than in the fully opened open position. This configuration makes it possible for the shut-off unit to be brought optionally into the intermediate position or into an intermediate position or into the open position when the pressure at the patient-side port is above the pressure limit, depending on how high this pressure is. The shut-off unit is also locked in the intermediate position and cannot be moved unintentionally. Pressure can be reduced from the patient-side port in the intermediate position as well.

According to the present invention, the shut-off unit is moved automatically from the closed position into the open position or into an open position when a pressure above the preset pressure limit is present at the patient-side port. In one embodiment, the optional actuating unit is connected to the shut-off unit such that the following effect is brought about: The actuating unit indicates the position in which the shut-off unit currently is. A manually performed actuation of the actuating unit moves the shut-off unit. Conversely, a movement of the shut-off unit, which is brought about automatically on the basis of the pressure that is present at the patient-side port, causes the actuating unit to move. For example, a longitudinal axis of the actuating unit is at right angles to the fluid direction of fluid through the valve arrangement when the shut-off unit is in the closed position or in the maximum possible closed position, and it is parallel to the flow direction when the shut-off unit is in the open position. This configuration indicates in an especially intuitive manner whether the shut-off unit is in the closed position or in the open position.

In one embodiment, the event that the shut-off unit is moved into the open position based on a pressure present at the patient-side port triggers the step of automatically generating an alarm and of outputting said alarm in a manner perceptible for a human being. For example, an event sensor automatically detects the event that the pressure present at the patient-side port is above the pressure limit, which triggers the alarm. In particular, a human being is informed by the alarm if the patient is coughing or intensely exhaling and has caused thereby the shut-off unit to open. A pressure above the pressure limit, which pressure is present at the patient-side port, can frequently be detected more easily compared to a direct detection of coughing of the patient. In one configuration, this alarm is transmitted to a receiver located at a distance in space in a cable-based or wireless manner, e.g., by means of radio waves, and is outputted by this receiver or on a separate output unit.

In one configuration, a filter, especially a filter for viruses, microbes and/or liquid drops, is arranged in the fluid connection between the valve arrangement and the ventilator. This filter prevents viruses and microbes from entering the ventilator through the fluid connection. The valve arrangement makes it possible to close the shut-off unit and to lock it in the closed position, to replace the filter and then to open the shut-off unit again and to lock it in the open position. The shut-off unit is opened automatically in this situation as well when a pressure above the pressure limit is present at the patient-side port, for example, because the patient is coughing.

The configuration with the filter can be combined with the configuration just described, in which an alarm is generated and outputted. This alarm may give a reason to a human being to check the filter, because it is possible that the filter is clogged because of coughing and must be replaced.

In one configuration, the valve arrangement additionally comprises a pressure sensor. This pressure sensor measures the pressure that is currently present at the patient-side port. The pressure sensor measures the pressure present at least when the shut-off unit is in the closed position. For example, the pressure sensor measures a parameter for a force that acts on the shut-off unit in the closed position from the direction of the patient-side port. The shut-off unit and the pressure sensor together make it possible to briefly close the shut-off unit and to measure the pressure originating from the patient, which is present at the patient-side port. This measured pressure is a parameter of the intrinsic breathing activity of the patient. It is ensured in this application as well that the shut-off unit is opened automatically when needed, e.g., when the patient is coughing.

The pressure, which is present at the patient-side port and is measured, is preferably outputted in a form perceptible for a human being and/or is transmitted to a receiver located at a distance in space, for example, in a wired or wireless manner. A display unit at the ventilator or at the valve arrangement preferably displays the measured pressure. This configuration makes it easier to monitor the current state of the patient being ventilated mechanically even from a remote location.

According to the present invention, the shut-off unit can be moved from an open position into a closed position, in which the shut-off unit interrupts or at least reduces the fluid connection. The device-side port is connected or can be connected to a fluid carrying unit. For example, this fluid carrying unit connects the valve arrangement to a ventilator. In one configuration, this connection is connected mechanically to the shut-off unit, the connection being such that the following effect is achieved: The step of moving the shut-off unit into the closed position automatically severs the connection between the device-side port and the fluid carrying unit. For example, a snap holder or a spring holder is opened.

The present invention pertains, furthermore, to a fluid carrying arrangement, which comprises a valve arrangement according to the present invention and a fluid carrying unit. The device-side port of the valve arrangement is connected detachably to the fluid carrying unit and is in fluid connection with the fluid carrying unit at least from time to time. The fluid carrying unit is preferably separated from the valve arrangement when the shut-off unit is moved in the closing direction, especially as was described in the above paragraph.

In a preferred application, the fluid carrying unit connects the valve arrangement to a ventilator. The configuration with the automatic severing of the connection ensures that when the shut-off unit is blocked, no fluid connection is established between the ventilator and the patient, which is, as a rule, undesirable. The process of separating the patient from the ventilator requires only a single action to be performed manually, namely, the action of moving the shut-off unit into the closed position. This action separates the valve arrangement from the fluid carrying unit and ensures that an undesired fluid connection between the lungs of the patient and the environment is blocked.

The present invention pertains, furthermore, to a ventilation system, which comprises a ventilator and at least one fluid carrying unit, in one configuration a plurality of fluid carrying units. The fluid carrying unit or each fluid carrying unit is in fluid connection with the ventilator at least from time to time. A valve arrangement according to the present invention is associated with each fluid carrying unit. Each fluid carrying unit can be separated from the associated valve arrangement. The valve arrangement or each valve arrangement is, in addition, preferably in a fluid connection with a patient-side coupling unit. The valve arrangement thus provides a separation point, at which the patient-side coupling unit can be separated from the ventilator. The above-described advantages are achieved in this case.

The present invention will be described below on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
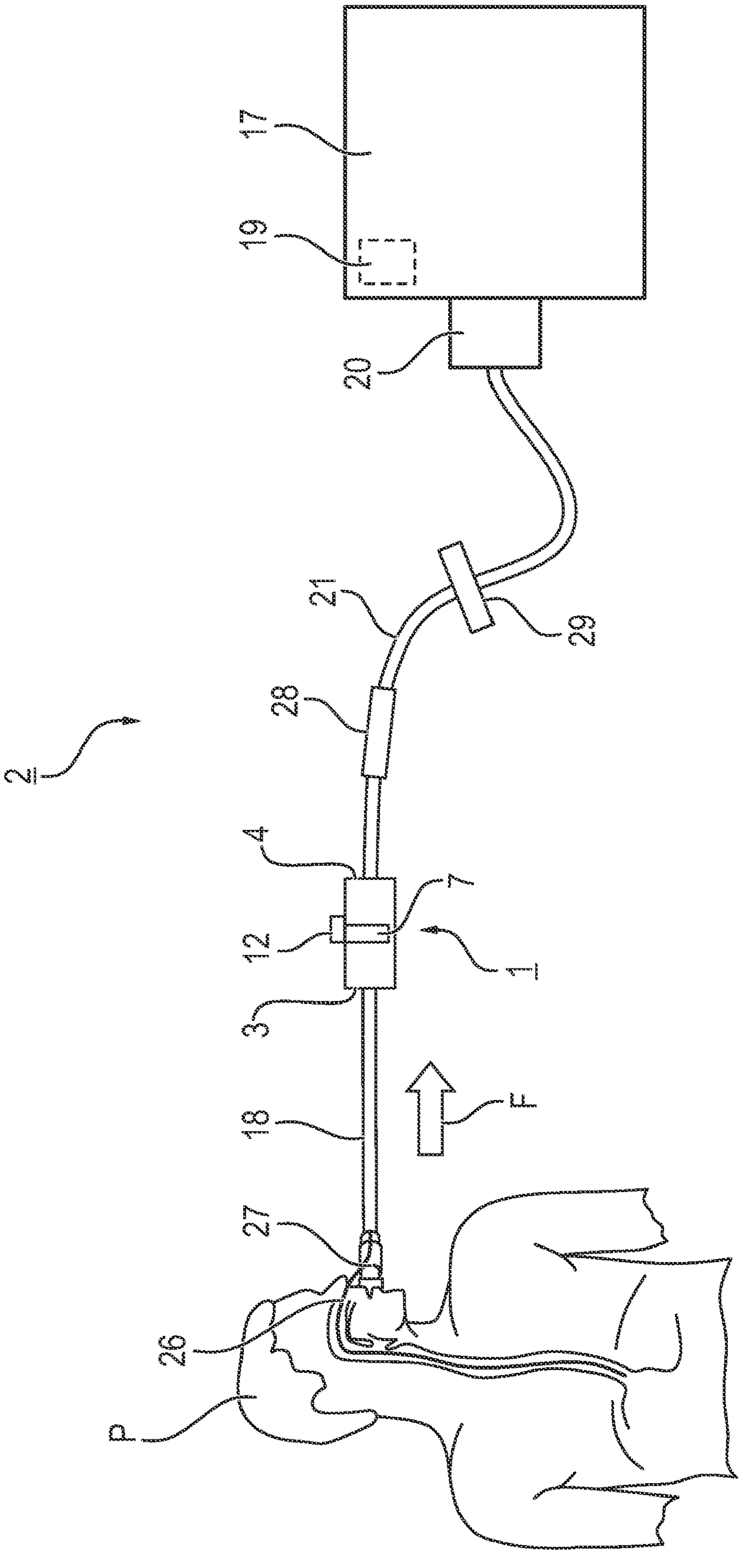
FIG. 1 is a schematic view showing an arrangement comprising a ventilator, a flexible tube system and a valve arrangement according to the present invention.

Referring to the drawings, the present invention is used in the exemplary embodiment in a fluid connection for the mechanical ventilation of a patient, optionally in a ventilation circuit. The patient is connected to a patient-side coupling unit, e.g., to a ventilation tube or to a breathing mask. The patient-side coupling unit is connected to a ventilator by means of a flexible tube system. The patient is ventilated mechanically by the ventilator by means of the fluid connection.

It is necessary from time to time during the treatment of the patient to interrupt this fluid connection between the patient-side coupling unit and the ventilator and thus to separate the patient-side coupling unit and hence the patient from the ventilator, for example, because cleaning or maintenance must be performed on the ventilator or because operating materials, especially a filter element, must be added or replaced or because the patient is transported from one ventilator to another ventilator. The patient is consequently uncoupled from the mechanical ventilation from time to time. The time period during which the patient is uncoupled from the mechanical ventilation is, as a rule, shorter than 3 minutes. The patient continues to be connected to the patient-side coupling unit during this separation as well.

There is a risk that the patient-side coupling unit and hence the lungs of the patient are in a fluid connection with the surrounding atmosphere after this uncoupling. This may cause the residual air pressure to drop in the lungs of the patient (positive end-expiratory pressure, PEEP). This could cause the lungs to collapse or an atelectasis to develop in some patients. The valve arrangement according to the present invention reduces this risk and maintains a residual air pressure (PEEP) in the lungs for a sufficiently long time in many cases.

FIG. 1 schematically shows a ventilation system 2, which ventilates a patient P mechanically at least from time to time and comprises the following components:

- a ventilator 17 with an optional receiving unit 19,
- an optional breathing air filter 20,
- a device-side breathing air tube 21,
- a valve arrangement 1 according to the present invention with a shut-off unit 7, which can be opened and closed,
- a patient-side breathing air tube 18,
- a part of a patient-side coupling unit 26, which part is located in the body of the patient, e.g., an endotracheal tube or a tracheal cannula or a catheter,
- a mouthpiece 27 at the patient-side end of the breathing air tube 18,
- a connection unit 28 in the device-side breathing air tube 21, which makes it possible to insert an intracorporeal device, e.g., a catheter or an endoscope, into the fluid connection, and
- a filter 29 against bacteria and viruses in the device-side breathing air tube 21.

The patient-side coupling unit comprises in the exemplary embodiment the part 26 located in the body and the mouthpiece 27. The patient-side coupling unit may also comprise a breathing mask.

The patient-side breathing air tube 18 establishes a fluid connection between the patient-side coupling unit 26, 27 and the valve arrangement 1, and the device-side breathing air tube 21 establishes a fluid connection between the ventilator 17 and the valve arrangement 1. The two breathing air tubes 18 and 21 belong to the fluid carrying system of the exemplary embodiment. Since an anesthetic can flow through the fluid connection in one embodiment, the components of the valve arrangement 1 are made of a material that is not attacked by anesthetic.

A device-side port 4 of the valve arrangement 1 is detachably connected to the device-side breathing air tube 21. The breathing air tube 21 can preferably be pushed over the device-side port 4, which may have a conical shape. The device-side port 4 preferably comprises a screw cap or snap closure, and the device-side breathing air tube 21 has a corresponding counterpiece at a patient-side end. The device-side breathing air tube 21 preferably comprises two parallel flexible tubes for inhalation and for exhalation, both of which are connected to the ventilator 17, a single flexible tube, which is connected to the device-side port 4 as well as a T-piece or Y-piece, which connects the parallel flexible tubes to this individual flexible tube. This configuration is not shown in FIG. 1.

A patient-side port 3 of the valve arrangement 1 is detachably or permanently connected to the patient-side breathing air tube 18. Air, which the patient P exhales, flows in a flow direction F through the patient-side breathing air tube 18 to the ventilator 17 when the patient P is exhaling. The patient-side breathing air tube 18 can preferably be pushed into the patient-side port 3. A ventilation stroke of the ventilator 17 causes air to flow against this flow direction F from the ventilator 17 to the mouthpiece 27 and farther into the part 26. It is also possible that the patient-side coupling unit 26, 27 can be connected directly to the patient-side port 3 and the patient-side breathing air tube 18 is not needed. A fluid connection is established between the valve arrangement 1 and the patient-side coupling unit 26, 27 in this case as well.

It is possible thanks to the valve arrangement 1 to sever the fluid connection between the patient-side breathing air tube 18 and the ventilator 17 at a separation point without a fluid connection becoming established between the patient-side breathing air tube 18 and the environment after the separation. The separation point is located in the exemplary embodiment between the two ports 3 and 4 of the valve arrangement 1, so that the patient-side breathing air tube 18 is detached from the device-side breathing air tube 21 after a separation. The valve arrangement 1 reduces the risk of collapse of the lungs of the patient P. As long as the valve arrangement 1 closes the patient-side breathing air tube 18, it is possible to separate the patient P from the ventilator 17 without the undesired fluid communication with the environment becoming established. It is possible to clean the ventilator 17 or to perform maintenance on it after the separation and to connect the patient P again to the ventilator 17 thereafter. It is also possible to transport the patient P to another device and then to connect the device-side port 4 to a breathing air tube or to another fluid carrying unit of this other device.

The receiving unit 19 will be explained below.

Figure 2:
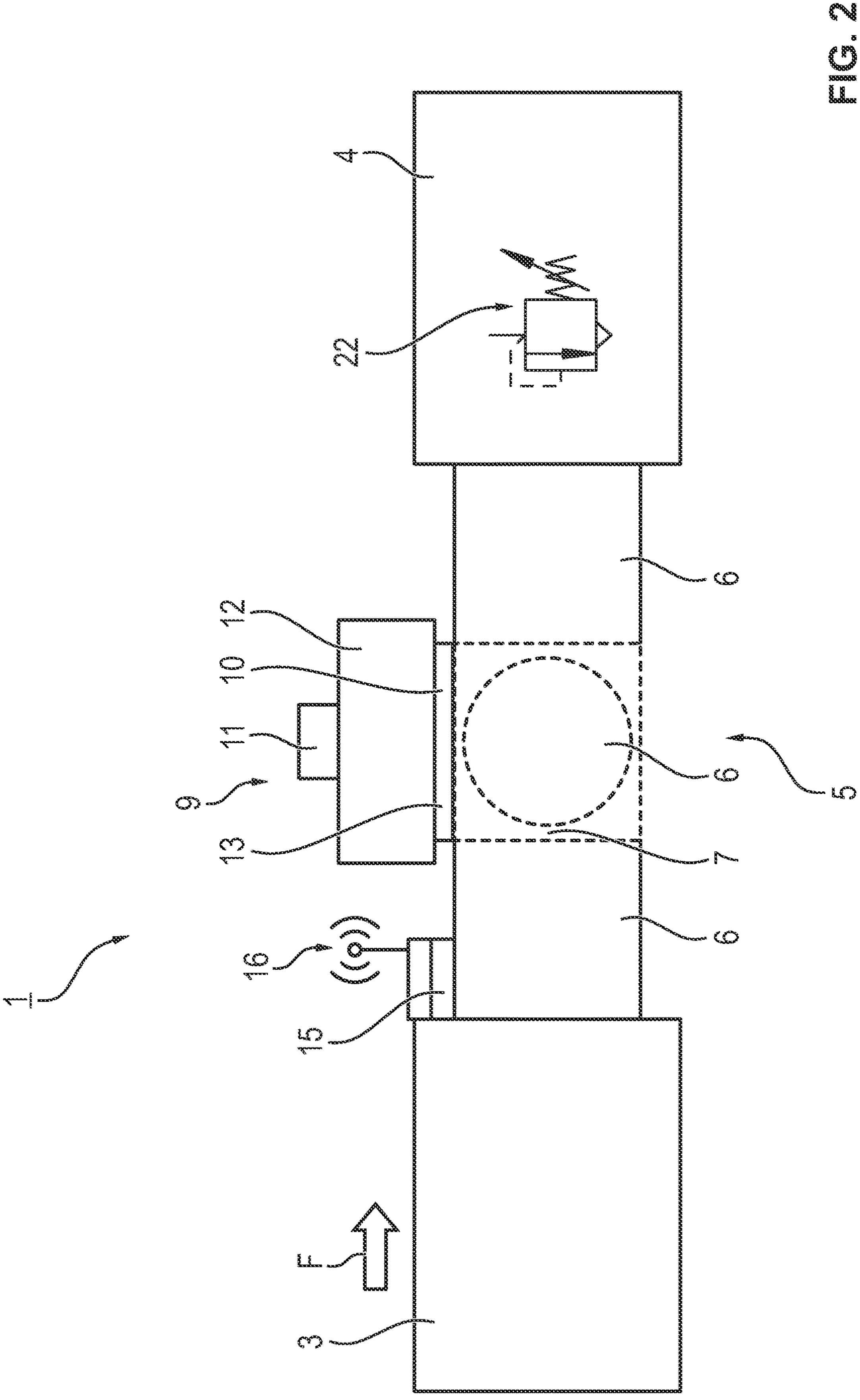
FIG. 2 is a schematic view showing the valve arrangement in the open position.
Figure 3:
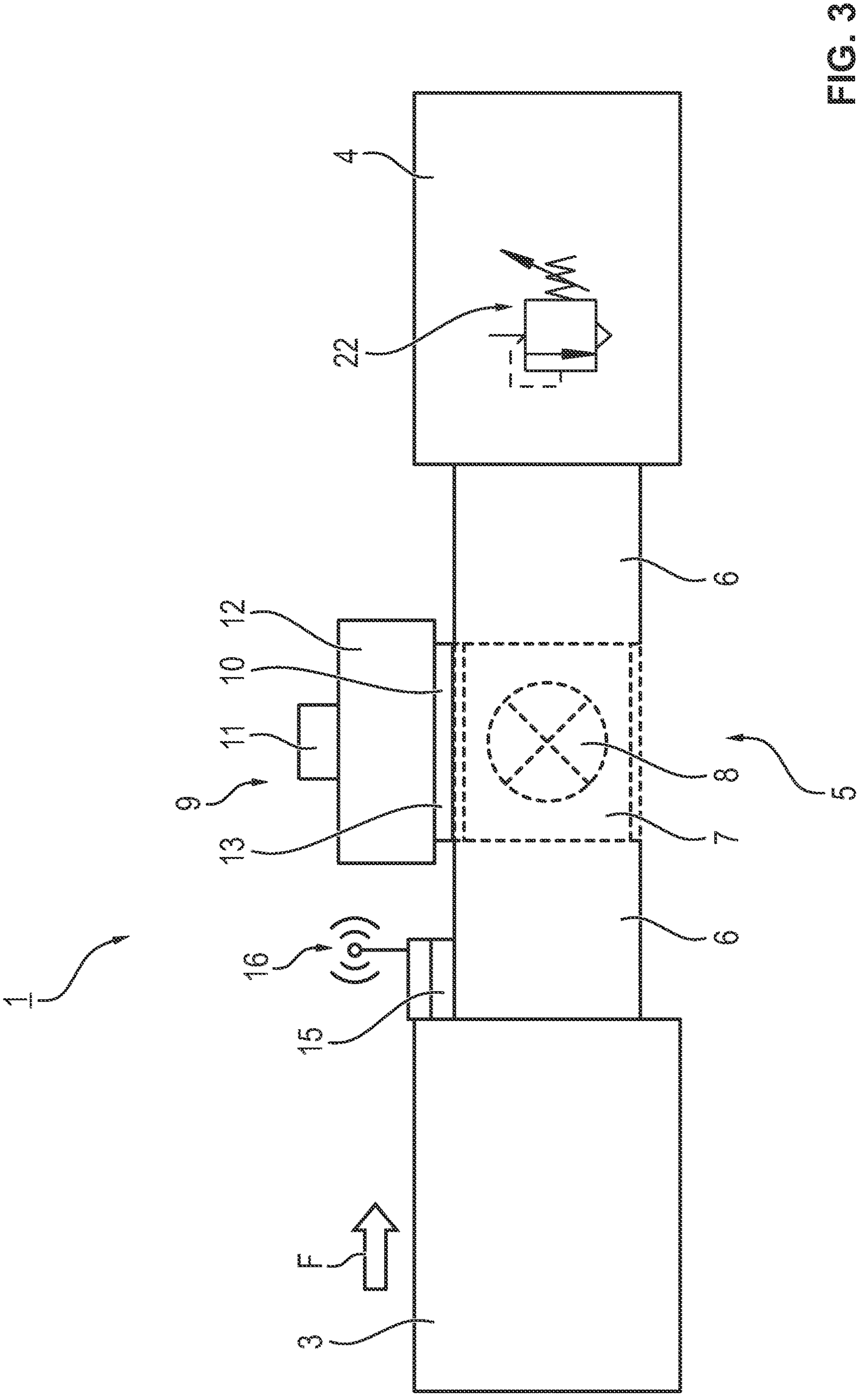
FIG. 3 is a schematic view showing the valve arrangement in the closed position.

FIG. 2 and FIG. 3 schematically show the valve arrangement 1 according to the exemplary embodiment. A tubular and preferably rigid fluid carrying unit 6 connects the patient-side port 3 to the device-side port 4 in a fluid-tight manner and preferably such that they are adapted to rotate in unison. A valve 5, which can be actuated manually, is arranged between the two ports 3 and 4 and it comprises a shut-off unit 7, which can be moved to and fro between an open position and a closed position, and an actuating unit 12 for the shut-off unit 7. In the open position (FIG. 2) the shut-off unit 7 makes it possible for fluid to flow through the fluid carrying unit 6, and it does not preferably influence the flow of fluid through the valve arrangement 1 thereafter. As long as the ventilator 17 is ventilating the patient P mechanically, the shut-off unit 7 is, as a rule, in the open position. In the closed position (FIG. 3), the shut-off unit 7 prevents fluid from flowing through the fluid carrying unit 6, or it at least reduces the volume flow through the fluid carrying unit 6 compared to the open position.

The shut-off unit 7 preferably comprises a rigid flat flap, an elastic membrane, a spring and/or a ball or another suitable shut-off element.

By means of the actuating unit 12 of the valve 5, a user can move the shut-off unit 7 from one position into the other position manually. The actuating unit 12 is preferably connected mechanically to the shut-off unit 7 and it can be moved to and fro between an open position and a closed position. The actuating unit 12 is permanently connected to the shut-off unit 7 in the exemplary embodiment and the two elements 7 and 12 cannot move relative to one another. The actuating unit 12 preferably snaps in, in each end position (open position and closed position), doing so perceivably for a user ("haptic feedback") and preferably also in an audible manner ("acoustic feedback"). Thanks to this configuration, a user notices that the actuating unit 12 is indeed in an end position.

The actuating unit 12 may also be configured as a remote control, which is connected to an adjusting member for the shut-off unit 7 by means of, e.g., a cable or by means of radio waves. A user can use the remote control 12 from a distant location in order to open and to close the shut-off unit 7.

If the actuating unit 12 is moved from the open position or from an open position into a closed position, this movement of the actuating unit 12 causes the shut-off unit 7 to be moved from the open position or from the corresponding open position into the closed position. The corresponding statement can be made for a movement in the reverse direction.

In one embodiment, an optional restoring element, not shown, for example, a spring, seeks to move the actuating unit 12 into the open position and to hold it in the open position. The actuating unit 12 can be moved into the closed position from the open position against the restoring force of this restoring element. This configuration reduces the risk of unintentionally moving the shut-off unit 7 into the closed position.

In one embodiment, the shut-off unit 7 or the actuating unit 12 is coupled mechanically to the device-side port 4. As soon as the shut-off unit 7 is moved into the closed position, the device-side breathing air tube 21 is automatically separated from the device-side port 4 and the device-side breathing air tube 21 can be pulled off. For example, a snap holder of the device-side port 4 is opened. A movement of the actuating unit 12 into the closed position preferably causes the device-side breathing air tube 21 to be automatically separated. This configuration reduces the risk of the ventilator 17 performing ventilation strokes with the valve 5 closed and of these ventilation strokes leading to a great increase in pressure in the closed device-side breathing air tube 21. This undesired situation could lead to damage to the ventilator 17 and/or to the breathing air tube 21.

A configuration in which the shut-off unit 7 can be moved into exactly one open position and be locked in this position will be described below. The term "the open position" is used therefore. Different open positions of the shut-off unit 7 are possible as well.

A locking unit 10, shown only schematically in FIG. 2 and FIG. 3, holds the shut-off unit 7 in an open locked state in the open position. In a closed locked state, the locking unit 10 holds the shut-off unit 7 in the closed position. The locking unit 10 consequently brings about a bistable state of the shut-off unit 7. The shut-off unit 7 is locked in both the open position and the closed position and cannot then be moved or it can be moved with a relative strong force only compared to a non-locked state. The locking unit 10 thus prevents the locked shut-off unit 7 from being unintentionally moved. This is true of both the shut-off unit 7 in the open position and of the shut-off unit 7 in the closed position. In particular, the locking unit 10 prevents the shut-off unit 7 from being moved unintentionally from one position into the other position or into an intermediate position because of vibrations, shocks or contacts or mechanical contacts and therefore from being unintentionally opened because the patient is coughing slightly.

In one configuration, the locking unit 10 is connected directly to the shut-off unit 7. In another configuration, the locking unit 10 is mechanically connected to the actuating unit 12. In the closed locked state the locking unit 10 holds the actuating unit 12 in the closed position. In the open locked state the locking unit 10 holds the actuating unit 12 in the open position. The actuating unit 12, which is locked in this manner, holds the shut-off unit in the closed position or in the open position.

In one configuration, a latching unit, which has, for example, a detent or another snap-in projection and a snap-in seat, belongs to the locking unit 10. The actuating unit 12 snaps in perceptibly and/or audibly when it reaches an end position, i.e., when it reaches the closed position or the open position, and it is then locked. This indicates to a user that an end position is reached. A possible visual display will be described below.

The locking unit 10 can, in addition, preferably be brought into a released state. When the locking unit 10 is in the released state, neither the shut-off unit 7 nor the actuating unit 12 is locked, the actuating unit 12 can be actuated, and the shut-off unit 7 can be brought from one position into the other position without having to overcome a locking effect. In one configuration, the locking unit 10 comprises an actuating element, e.g., the safety element 13 described below. In order to move the locking unit 10 from a locked state into the released state, a user must actuate this actuating element 13 beforehand.

In the exemplary embodiment, the shut-off unit 7 and the actuating unit 12 can be moved together by 90° between the two end positions. The locking unit 10 is preferably configured such that it brings about a limit angle ("turnover point"). As long as the angle between the current position and the open position of the shut-off unit 7 is below this limit angle, the locking unit 10 seeks to move the shut-off unit 7 into the open position to hold it in this position, i.e., it is in the open locked state. If this angle is greater than the limit angle, the locking unit 10 seeks to bring the shut-off unit 7 into the closed position and to hold it in this position, i.e., it is in the closed locked state.

A safety element 13, which is likewise shown only schematically, holds in an inoperative position the locking unit 10 in the open locked state. A spring or another suitable restoring element exerts a restoring force, which holds the safety element 13 in this inoperative position. A user can actuate the safety element 13 against the restoring force. After an actuation of the safety element 13, the locking unit 10 is in the released state or can be moved into the released state. This configuration leads to a further reduction of the risk that the shut-off unit 7 would unintentionally or accidentally be moved or move by itself out of the open position and into the closed position. In order to move the shut-off unit 7 into the closed position, a user must at first move the safety element 13 against the restoring force from the inoperative position and then actuate the actuating unit 12.

It is possible that the patient P is coughing more intensely or exhales forcibly in another manner while the shut-off unit 7 is locked in the closed position. This situation leads to an increase in pressure at the closed patient-side port 3. The patient P could suffer serious health damage in the lungs, especially a barotrauma, if this pressure is not reduced rapidly. In addition, the shut-off unit 7 may remain in the closed position due to a defect or by mistake, even though the patient P can be in a fluid communication with the environment without risk.

In order to reduce these risks for the patient P, the valve arrangement 1 comprises in one configuration an optional pressure relief mechanism 8, which is likewise shown only schematically in FIG. 2 and in FIG. 3. This pressure relief mechanism 8 operates as follows:

When the shut-off unit 7 is in the closed position, the locking unit 10 is in the closed locked state and holds the shut-off unit 7 in the closed position. If a pressure, which is above a preset pressure limit, is present at the patient-side port 3 in this situation, the now activated pressure relief mechanism 8 automatically moves the shut-off unit 7 into the open position. The pressure relief mechanism 8 now overcomes a locking effect, for example, a restoring force or locked position, which the locking unit 10 exerts in the closed locked state, and this locking effect seeks to hold the shut-off unit 7 in the closed position.

The movement, which is elicited by the pressure at the patient-side port 3 and/or by the pressure relief mechanism 8, preferably causes the locking unit 10 to be moved into the open locked state and to hold now the shut-off unit 7 in the open position. This preferred configuration prevents the shut-off unit 7 from oscillating to and fro between the closed position and at least one intermediate position while the patient P is coughing. The shut-off unit 7 is rather locked in the open position, so that the patient P can cough undisturbed and also inhale without an undesired pressure building up.

In one configuration, the pressure relief mechanism 8 acts directly on the shut-off unit 7. In a preferred configuration, the pressure relief mechanism 8 acts, by contrast, on the actuating unit 12. When the shut-off unit 7 is in the closed position, the actuating unit 12 is in the closed position. The activated pressure relief mechanism 8 moves the actuating unit 12 automatically into the open position. The mechanical connection between the actuating unit 12 and the shut-off unit 7 causes the elicited movement of the actuating unit 12 to be transmitted to the shut-off unit 7 and the shut-off unit 7 to be moved against the locking effect of the locking unit 10 into the open position.

When the pressure at the patient-side port 3 is below this pressure limit, the pressure relief mechanism 8 does not affect the shut-off unit 7 or the locking unit 10. In particular, the pressure relief mechanism 8 allows the locking unit 10 to be in the closed locked state even if the pressure that is preset at the device-side port 4 is above the pressure limit.

As was just described, the valve arrangement 1 and especially the optional pressure relief mechanism 8 operate depending on the preset pressure limit. The preset pressure limit is preferably between 50 mmHg and 70 mmHg, especially preferably 60 mmHg. Many ventilators and other medical devices are coordinated with valves that open at 60 mmHg. The pressure limit is markedly higher than the residual air pressure that shall be maintained in the lungs (PEEP) and that is between 4 mmHg and 10 mmHg in adults. A user can change this pressure limit manually by means of an optional adjusting unit 11. The adjusting unit 11 comprises, for example, a handwheel as well as an indicator unit, for example, a dial, which shows the pressure limit currently set.

In one configuration, the adjusting unit 11 makes it possible to change the pressure limit continuously within a range. In a preferred embodiment, only a finite number of different values can be set by means of the adjusting unit, preferably at an increment of 10 mmHg, especially preferably to one of the four values 40 mmHg, 50 mmHg, 60 mmHg and 70 mmHg. The adjusting unit 11 preferably locks in each setting and holds the pressure limit at the set value. The adjusting unit 11 is prevented thereby from being moved accidentally and by the pressure limit is prevented from being changed thereby unintentionally.

The valve arrangement 1 optionally comprises, in addition to the pressure relief mechanism 8, a pressure relief valve 22, which is arranged, for example, in the device-side port 4. If a pressure that is above a preset overpressure limit occurs in the fluid connection between the patient P and the ventilator 17, this pressure relief valve 22 opens from time to time and releases pressure into the environment, preferably until the pressure is again below the overpressure limit. This overpressure limit is preferably above the pressure limit for the shut-off unit 7. Such an overpressure may develop, for example, when the ventilator 17 is activated and starts the ventilation, even though the shut-off unit 7 is in the closed position, or in case of a mechanical defect, which leads to blocking of the fluid connection.

The optional pressure relief valve 22 prevents, in particular, the ventilator 17 from exposing the patient P to an excessively high pressure during the mechanical ventilation. Furthermore, this pressure relief valve 22 reduces an overpressure when the ventilator 17 carries out ventilation strokes with the valve 5 closed or when the patient P is coughing or is inhaling forcefully in another manner during the mechanical ventilation, i.e., while the shut-off unit 7 is in the open position. The overpressure limit of this pressure relief valve 22 can preferably be set. The pressure relief valve 22 preferably comprises a restoring element, which seeks to bring the pressure relief valve 22 into a closed position and to hold it in this closed position. In one configuration, the pressure relief valve 22 opens against the force of the restoring element when a pressure above the overpressure limit is present, and it closes again when the pressure present drops below a lower additional overpressure limit. The pressure relief valve 22 preferably opens at a pressure above the overpressure limit, regardless of which side the pressure is present on.

The valve arrangement 1 optionally comprises, furthermore, a pressure sensor 15 and a transmitting unit 16. The pressure sensor 15 measures the pressure that is present at the patient-side port 3 at least when the shut-off unit 7 is closed. For example, the pressure sensor 15 measures a parameter for the force that is exerted from the patient-side port 3 on the shut-off unit 7 in the closed position. When the shut-off unit 7 is in the open position or in an open position, the pressure sensor 15 does not preferably measure a pressure. The valve arrangement 1 makes it therefore possible in many cases to embody a pressure sensor in an especially simple manner.

A measured value from the pressure sensor 15 is transmitted to the transmitting unit 16. The transmitting unit 16 transmits a measured value, which it received from the pressure sensor 15, to at least one receiver located at a distance in space, doing so preferably in a wireless manner by means of radio waves. The pressure measured value can then also be transmitted when the device-side breathing air tube 21 is separated from the valve arrangement 1. It is also possible that the measured value is transmitted in a wired manner.

FIG. 1 shows as an example a receiving unit 19 at the ventilator 17, which receiving unit receives a pressure measured value transmitted in a wireless manner. This pressure measured value is displayed, for example, on a display unit, not shown. The receiver or a receiver, which is located at a distance in space, may also be, for example, a mobile device, e.g., a Smartphone, a vibration wristband or a receiver of a stationary display unit.

Instead of the pressure sensor 15 or in addition to the pressure sensor 15, it is also possible to provide an event sensor, which automatically detects the event that the pressure at the patient-side port 3 has exceeded the preset pressure limit. If this event is detected, an alarm is triggered. As a response to this alarm, for example, a human being observes the patient P or checks the filter 29.

As was mentioned already, the optional pressure relief mechanism 8 moves the shut-off unit 7 from the closed position into the open position when the pressure at the patient-side port 3 is above the pressure limit. In one configuration, this pressure limit is selected to be such that the pressure present at the patient-side port 3 is not sufficient alone to overcome the locking effect of the locking unit 10 and to move the shut-off unit 7 or even the actuating unit 12 against this locking effect. The pressure relief mechanism 8 therefore preferably comprises an adjusting member. This adjusting member is capable of moving the shut-off unit 7 against the locking effect into the open position. The adjusting member is activated when the pressure present is above the pressure limit.

Figure 4:
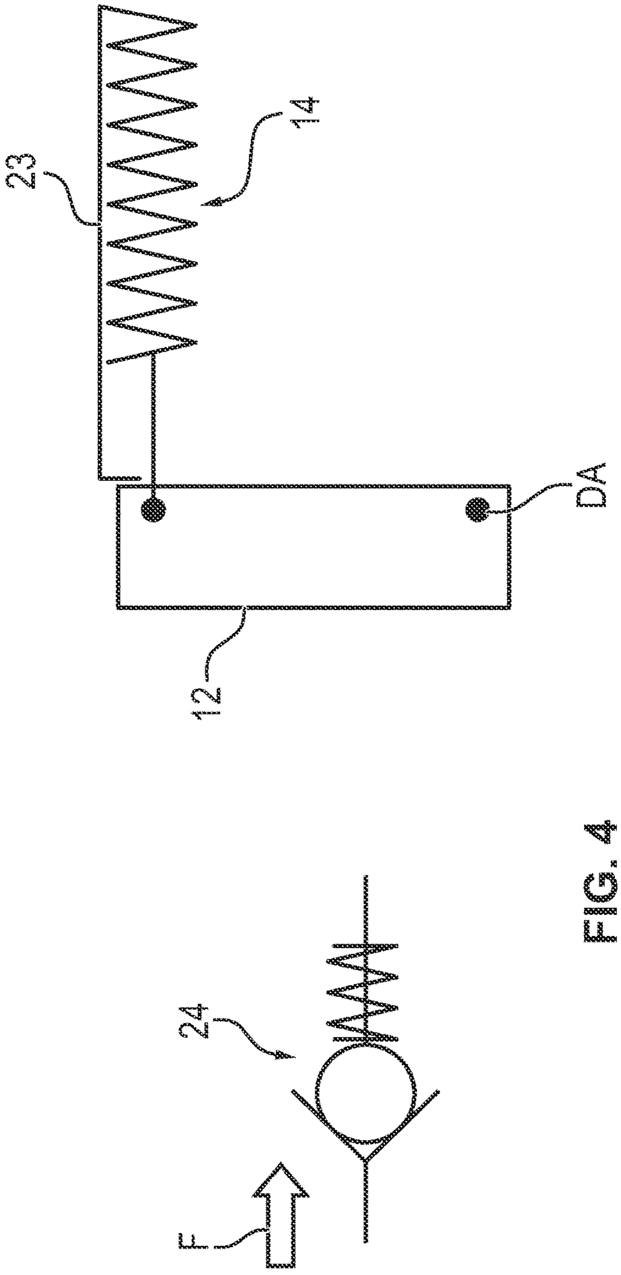
FIG. 4 is a schematic view showing a purely mechanically configured pressure relief mechanism with a locking body in the locked position.
Figure 5:
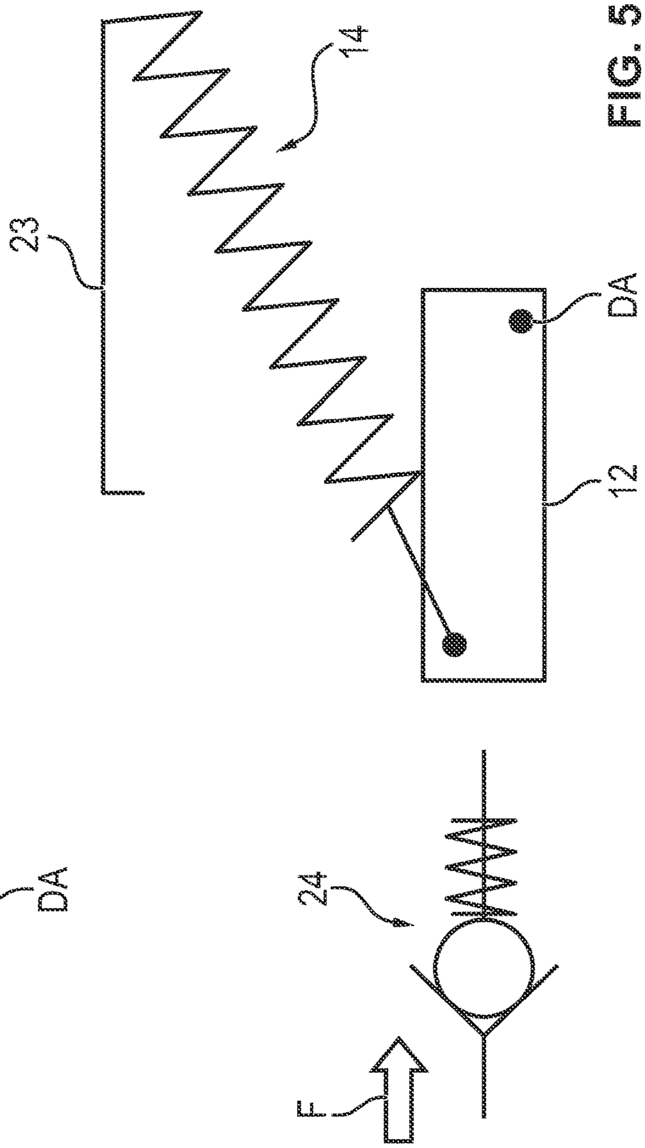
FIG. 5 is a schematic view showing the pressure relief mechanism according to FIG. 4 with the locking body in the released position.

FIG. 4 and FIG. 5 schematically show an exemplary, purely mechanical embodiment of the pressure relief mechanism 8. As was mentioned already, a movement of the actuating unit 12 from the closed position into the open position causes the shut-off unit 7 to be moved from the closed position into the open position. The actuating unit 12 is connected mechanically to the shut-off unit 7, preferably such that the actuating unit 12 cannot move relative to the shut-off unit 7. For example, the actuating unit 12 can be moved about the axis of rotation 25.

In the example shown, the adjusting member has the form of a compression spring 14, which is shown in a tensioned state in FIG. 4 and in a relaxed state in FIG. 5. The actuating unit 12 is in the closed position in FIG. 4 and in the open position in FIG. 5. The compression spring 14 is pretensioned when the actuating unit 12 is rotated from the open position into the closed position and it moves thereby the shut-off unit 7 into the closed position. A movement of the compression spring 14 from the tensioned state into the relaxed state moves the actuating unit 12 against the locking effect of the locking unit 10 from the closed position into the open position. This movement of the actuating unit 12 causes the shut-off unit 7 to be moved from the closed position into the open position.

A locking body 23, shown schematically, holds in a locked position the compression spring 14 in the tensioned state. When the actuating unit 12 is rotated into the closed position and the compression spring 14 is tensioned thereby, the locking body 23 snaps in. In the released position, the locking body 23 releases the compression spring 14, which causes the compression spring 14 to become abruptly relaxed and to turn thereby the actuating unit 12 about the axis of rotation DA and to move it thereby into the open position. A triggering component, e.g., a nonreturn valve 24, is capable of moving the locking body 23 from the locked position into the released position. The triggering component 24 is configured such that it moves the locking body 23 into the released position when the pressure present at the patient-side port 3 reaches or exceeds the pressure limit. The triggering element 24 and/or the compression spring 14 are preferably arranged in the patient-side port 3.

Figure 7:
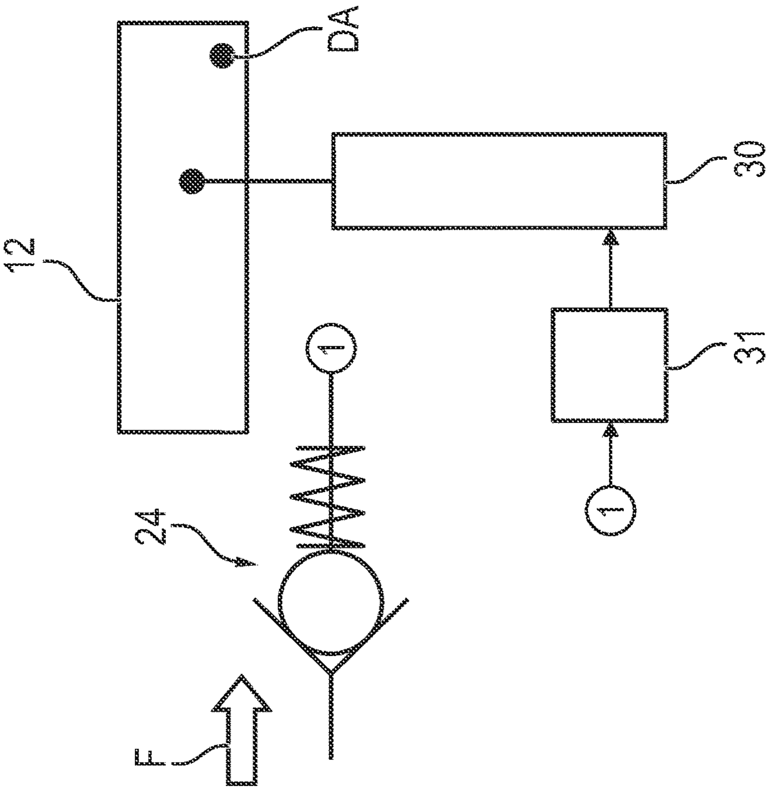
FIG. 7 is a schematic view showing the pressure relief mechanism according to FIG. 6 with the actuating element in the open position.
Figure 6:
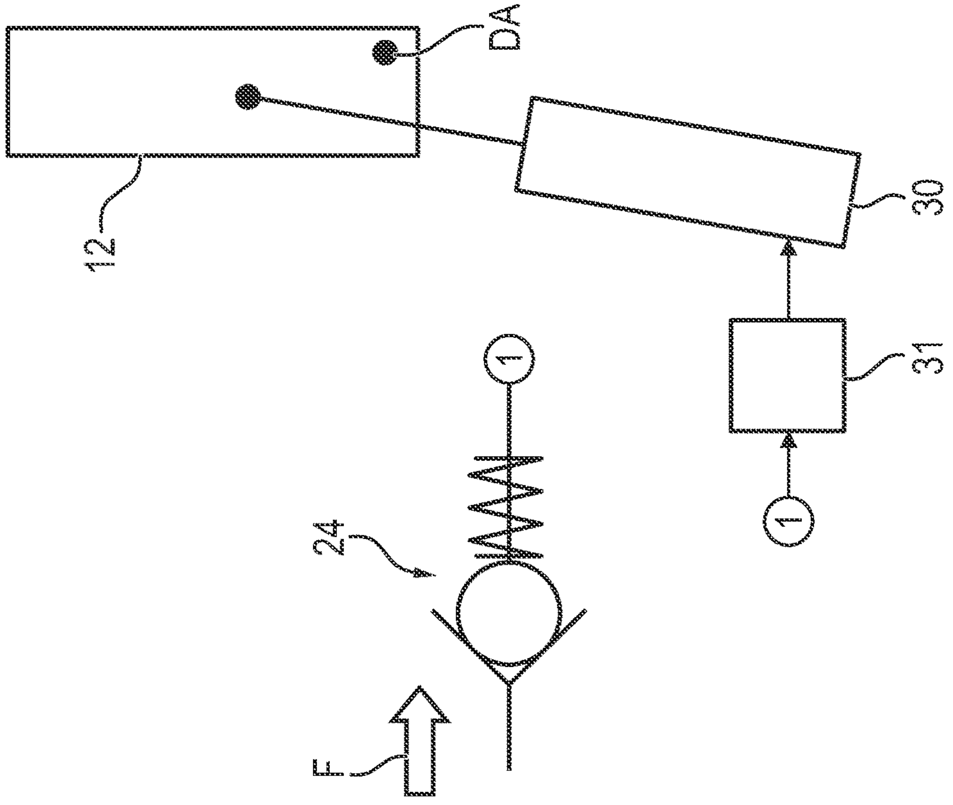
FIG. 6 is a schematic view showing a pressure relief mechanism with an actuatable adjusting member for the actuating element, wherein the actuating element is in the closed position.

In another configuration, the adjusting member has an electrical or pneumatic or hydraulic configuration and can be actuated from the outside or by the triggering element 24. FIG. 6 and FIG. 7 schematically show a corresponding implementation. The triggering component 24 generates a signal when the pressure at the patient-side port 3 is above the pressure limit. This signal is transmitted to a control device 31. The control device 31 actuates an adjusting member 30, in this case a double-acting piston-and-cylinder unit. The actuated adjusting element 30 rotates the actuating element 12 about the axis of rotation DA from the closed position (FIG. 6) into the open position (FIG. 7).

In another implementation, the control device 31 receives a pressure measured value, which the pressure sensor 15 has measured and transmitted with the shut-off unit 7 closed. This control device 31 actuates the adjusting member 30 when the measured value is above the pressure limit. The actuated electrical or pneumatic or hydraulic adjusting member 30 moves the actuating unit 12 from the closed position into the open position or it moves the shut-off unit 7 directly from the closed position into the open position. The configurations with the mechanical pressure relief mechanism (FIG. 4 and FIG. 5) and with the actuatable adjusting member (FIG. 6 and FIG. 7) may be combined, for example, in order to create redundancy.

Figure 8:
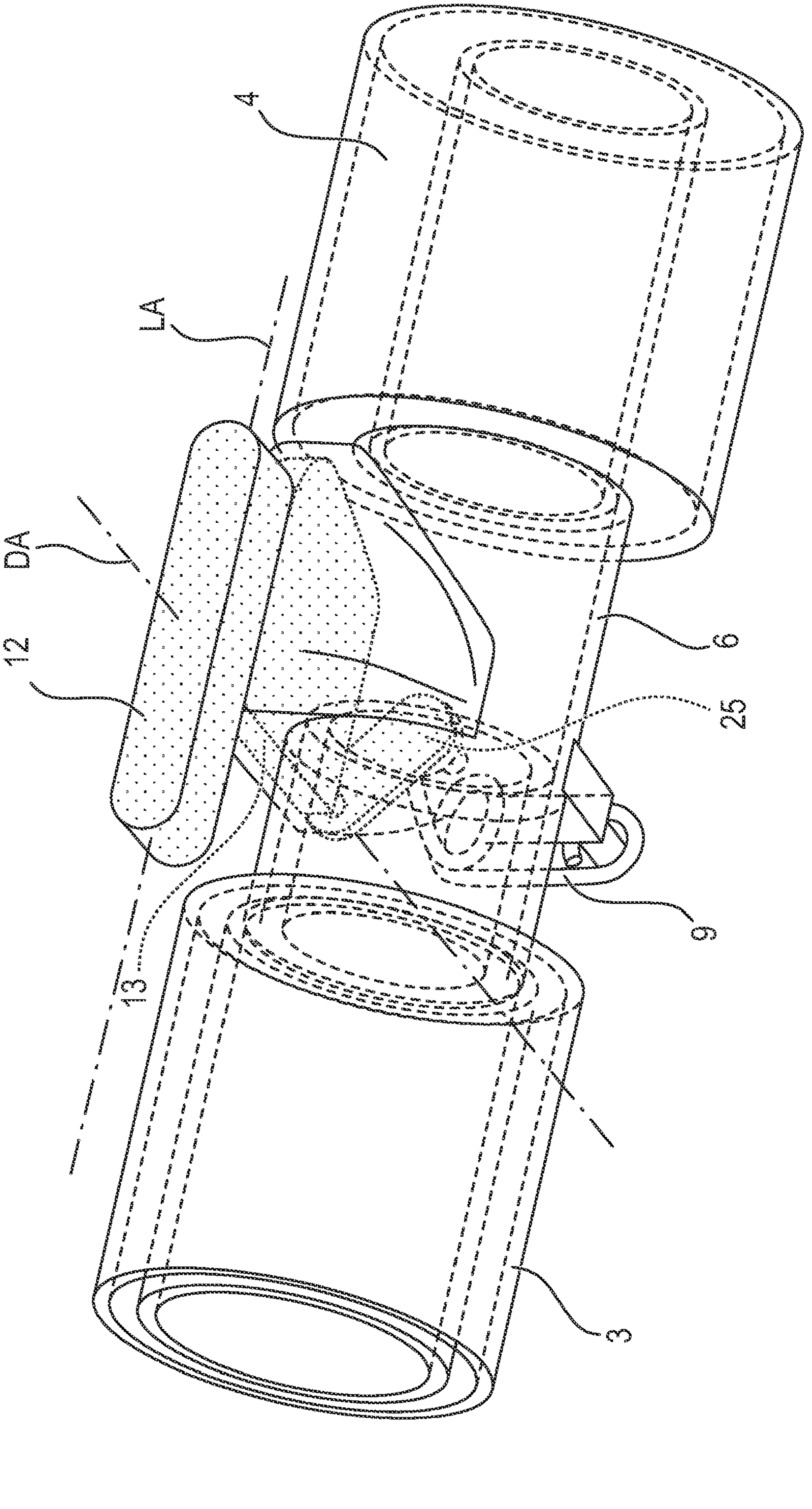
FIG. 8 is a schematic view showing an embodiment of the valve arrangement in a perspective view with the shut-off unit in the open position.
Figure 9:
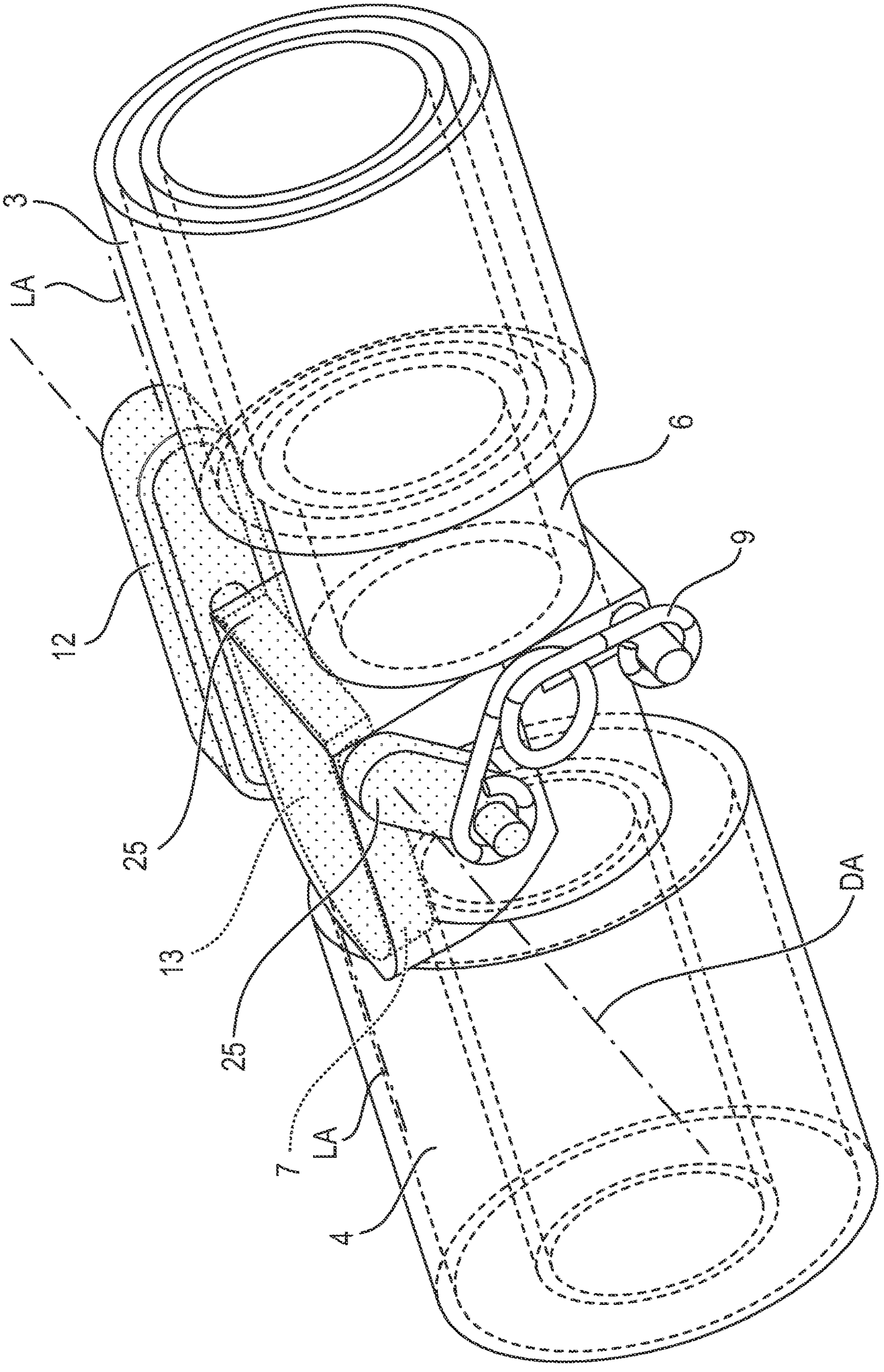
FIG. 9 is a schematic view showing the configuration according to FIG. 8 from the other side.
Figure 10:
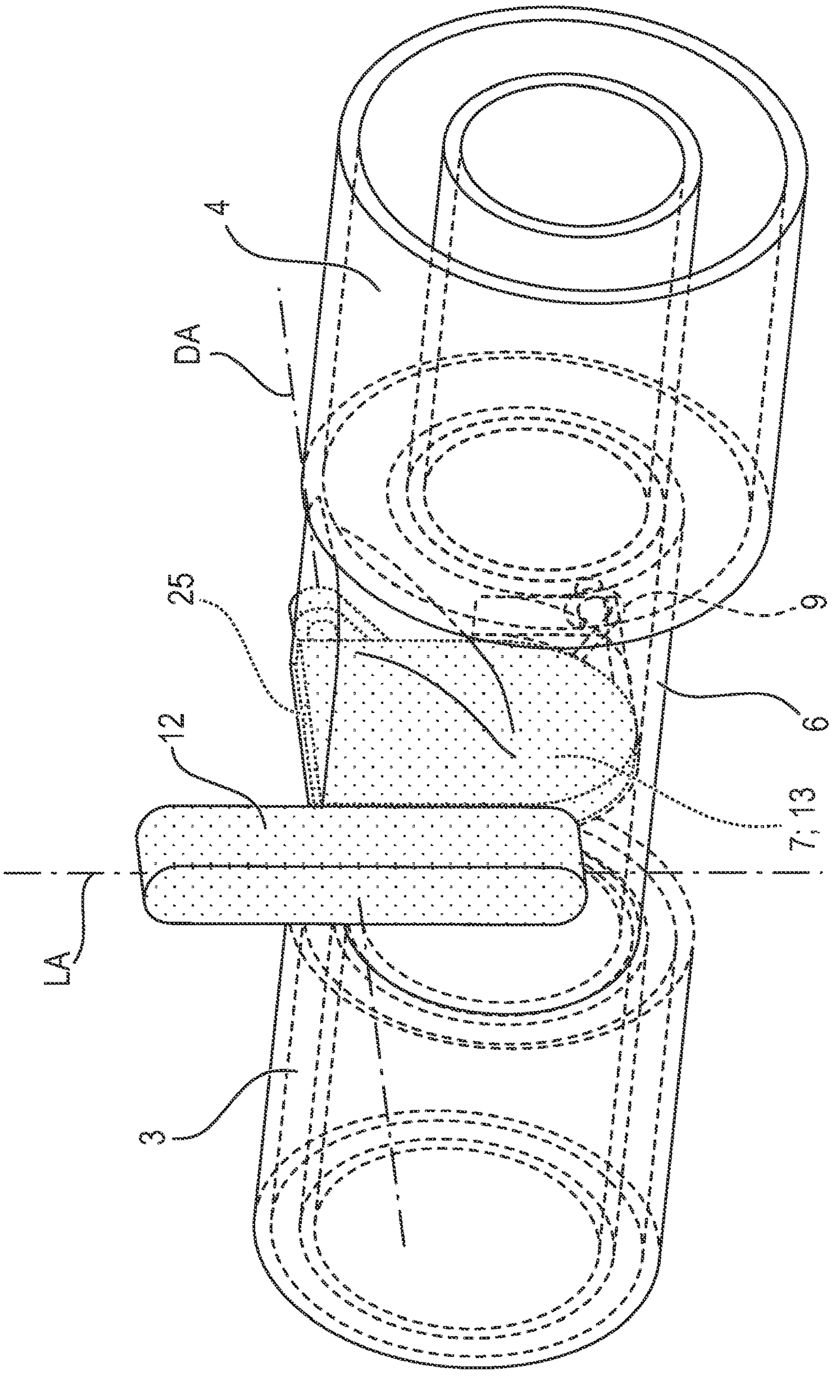
FIG. 10 is a schematic view showing the configuration from the viewing direction of FIG. 8 with the shut-off unit in the closed position.
Figure 11:
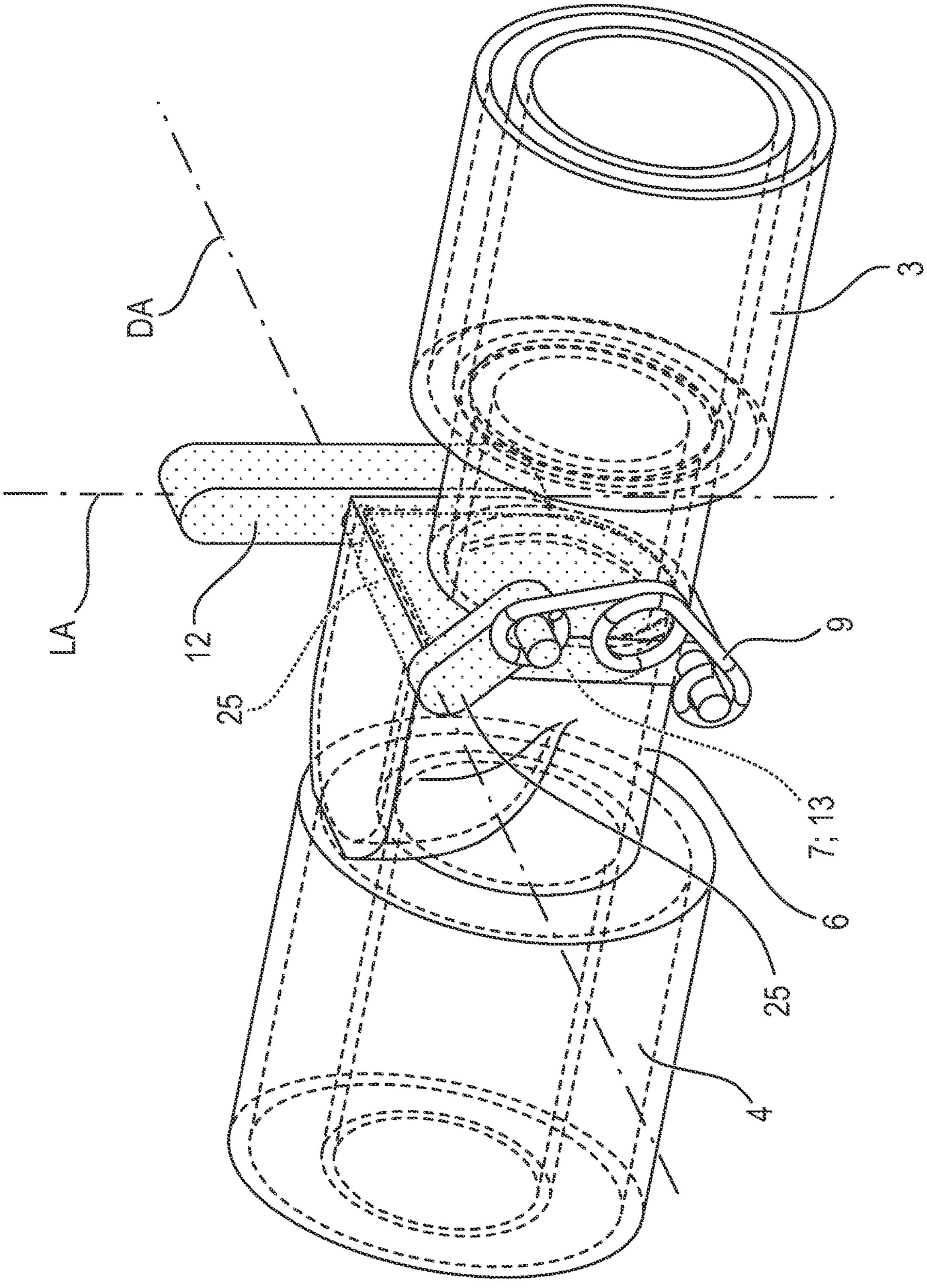
FIG. 11 is a schematic view showing the configuration from the viewing direction of FIG. 9 with the shut-off unit in the closed position.
Figure 12:
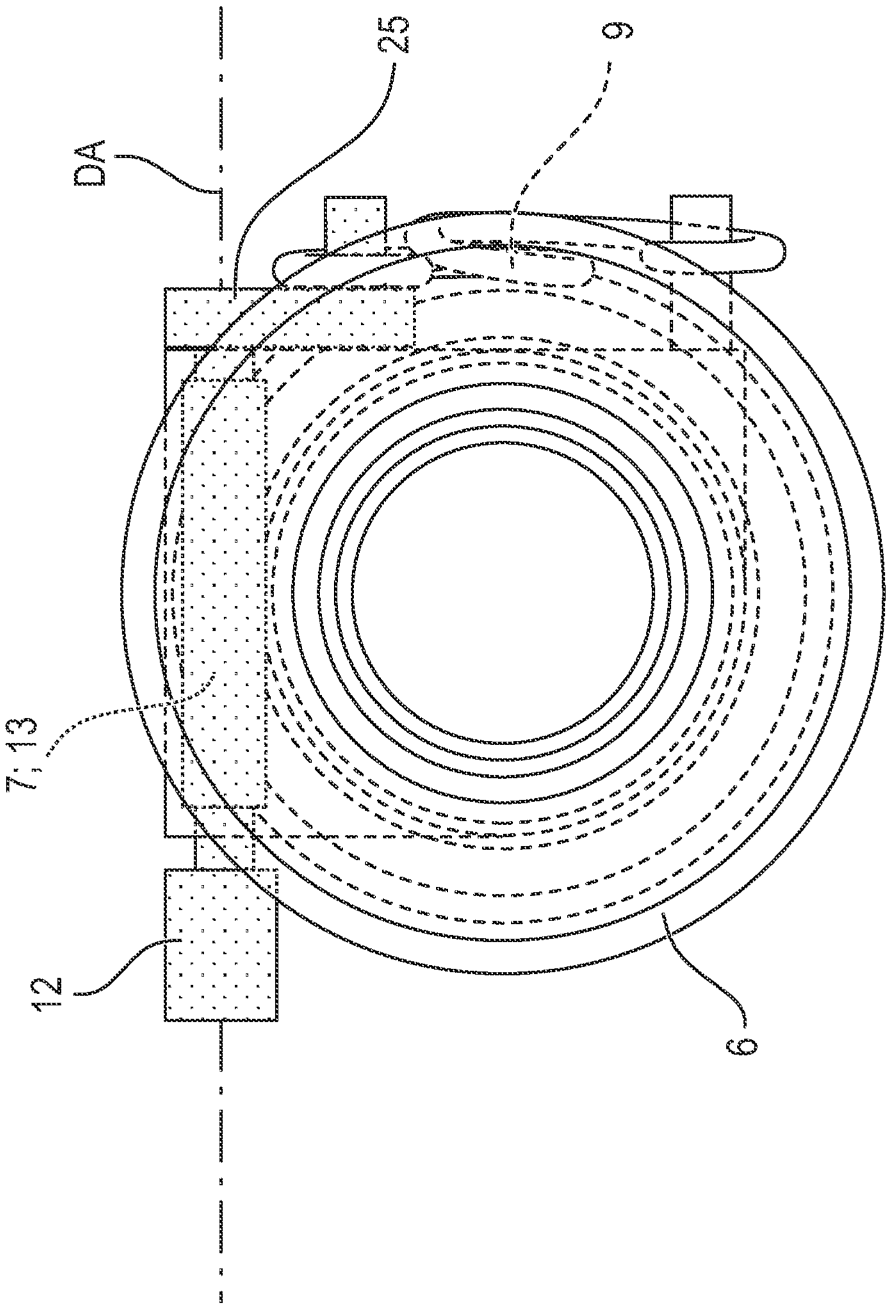
FIG. 12 is a schematic view showing a cross-sectional view through the configuration according to FIG. 8 through FIG. 11 with the shut-off unit in the open position.
Figure 13:
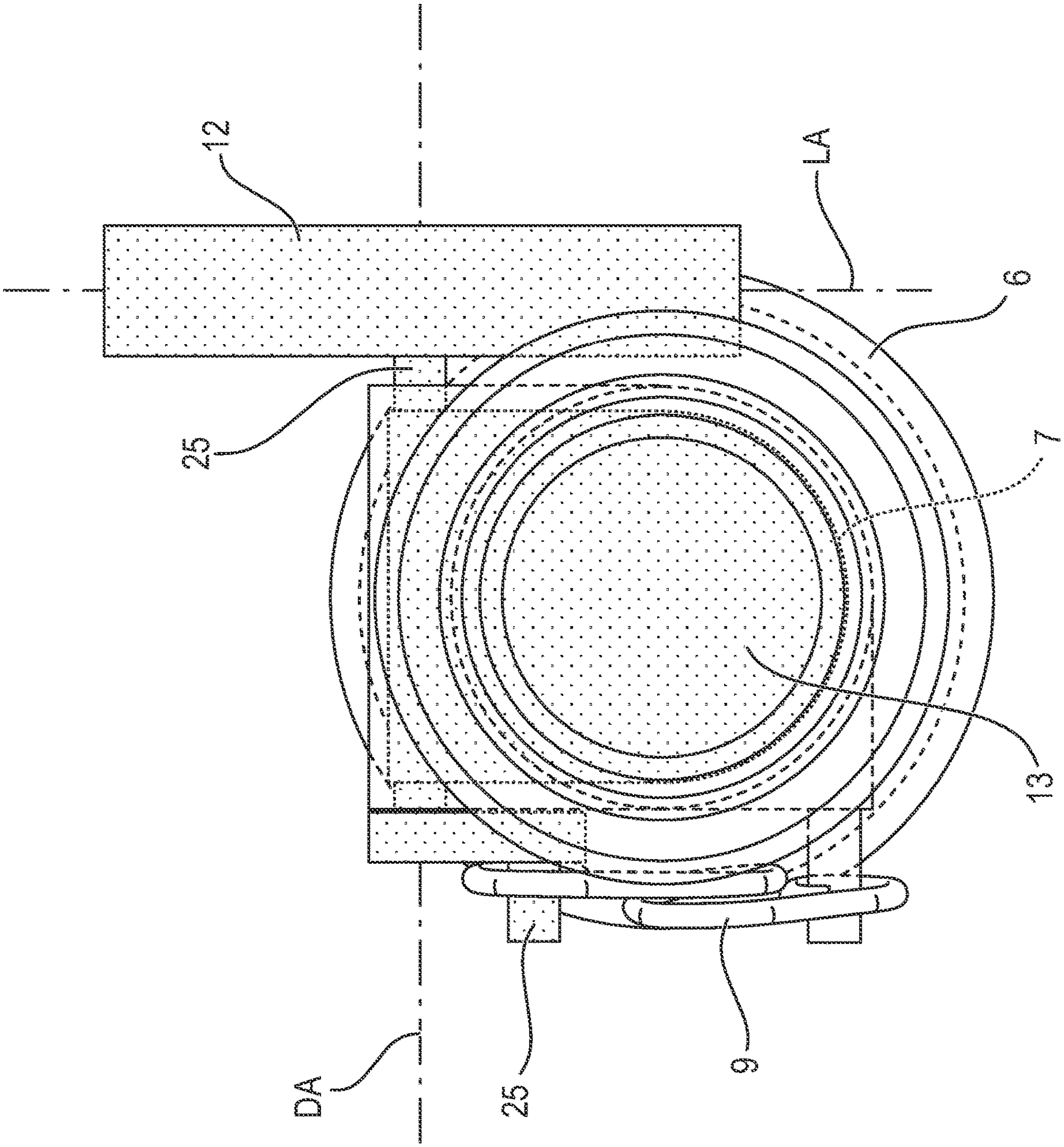
FIG. 13 is a schematic view showing a cross-sectional view through the configuration according to FIG. 8 through FIG. 11 with the shut-off unit in the closed position.

FIG. 8 through FIG. 13 show an exemplary configuration of the valve arrangement 1 from different viewing directions, the pressure relief mechanism 8 being omitted. FIG. 8, FIG. 9 and FIG. 12 show the actuating unit 12 in the open position and hence the shut-off unit 7 in the open position, and FIG. 10, FIG. 11 and FIG. 13 show the actuating unit 12 in the closed position and hence the shut-off unit 7 in the closed position.

The actuating unit 12 extends along a longitudinal axis LA and can be rotated in both directions about the axis of rotation DA, doing so by 90° between two end positions. The position of the actuating unit 12 shows visually whether the shut-off unit 7 is in the open position or in the closed position. When the shut-off unit 7 is in the open position, the longitudinal axis LA of the actuating unit 12 is parallel to the longitudinal axis of the fluid carrying unit 6, as this is shown in FIG. 8 and FIG. 9. If the shut-off unit 7 is in the closed position, the longitudinal axis LA of the actuating unit 12 is at right angles to this longitudinal axis LA, as this is shown in FIG. 10 and FIG. 11. Thanks to this configuration, the actuating unit 12 intuitively indicates the current position of the shut-off unit 7. This configuration is a purely mechanical one and requires no additional display unit. The actuating unit 12 rather acts itself as a display unit. The actuating unit 12 preferably has, in addition, a color different from that of the rest of the valve arrangement 1, having, for example, a bold red color. It is possible that the surface of the actuating unit 12 is provided with a phosphorescing or fluorescing material in order for the position of the actuating unit 12 to also be able to be readily recognized in the dark or under poor light conditions.

The shut-off unit 7 comprises in this configuration a flat element, which is mechanically connected to the actuating unit 12, for example, a disk, which has two parallel circular end faces or a flat end face and a convex end face or two parallel and outwardly bent end faces. This flat element blocks the fluid carrying unit 6 in the closed position. This flat element releases the fluid carrying unit 6 in the open position. The jacket surface of the flat element is preferably adapted to the inner wall of the fluid carrying unit 6, so that only a small gap develops between the flat element and the fluid carrying unit 6 when the shut-off unit 7 is in the closed position. This configuration eliminates the need for a separate sealing element.

In the configuration with the convex end face, the flat element of the shut-off unit 7 may be configured such that the shut-off unit 7 is congruent flush with the outer profiles of the two ports 3 and 4 in the open position. In the configuration with the two parallel and outwardly bent end faces, the flat element may be configured such that the shut-off unit 7 is congruent flush with the inner wall of the fluid carrying unit 6.

The locking unit 10 comprises a mechanical connection element 25 and a spring 9. The connection element 25 mechanically connects the actuating unit 12 to the spring 9. The spring 9 is connected on one side to the connection element 25 and is supported on the other side at the tubular fluid carrying unit 6. The spring 9 holds the actuating unit 12 in both the open position and the closed position. The locking unit 10 acts via the mechanical connection element 25 on the shut-off unit 7 and hence on the actuating unit 12.

FIG. 12 and FIG. 13 show the valve arrangement 1 in a cross-sectional view. The flow direction F of the fluid is at right angles to the drawing plane of FIG. 12 and FIG. 13.

The outer profile of the shut-off unit 7 is preferably adapted to the inner profile of the preferably tubular fluid carrying unit 6. The shut-off unit 7 closes the fluid carrying unit 6 completely in the closed position in this configuration. In one configuration, a sealing element, for example, a rubber ring or an O-ring, is arranged on the inner wall of the fluid carrying unit 6 and/or on the outer wall of the shut-off unit 7. This sealing element is preferably made of a material that is not attacked by an anesthetic. In another configuration, the fluid carrying unit 6 is closed, preferably in a positive-locking manner, solely by the shut-off unit 7, and a separate sealing element is not needed. This configuration eliminates the need to fasten a sealing element at the fluid carrying unit 6 or at the shut-off unit 7.

Both the fluid carrying unit 6 and the shut-off unit 7 are preferably made of a hard plastic, optionally of a transparent plastic. Thanks to this configuration, the parts 6 and 7 can be manufactured in a short time, for example, by an injection molding process, and they can be cleaned, if needed, in a short time.

The shut-off unit 7 is preferably arranged such that the shut-off unit 7 is fully outside the fluid carrying unit 6 in the open position. The entire cross-sectional area of the fluid carrying unit 6 is available for the flow of fluid in this configuration. The risk of swirling at the opened shut-off unit 7 is ruled out or is at least reduced. Such a swirling may lead to a greatly varying flow of fluid, and this can, in turn, lead to a volume flow sensor yielding unreliable results. Therefore, the spontaneous breathing of the patient P can only to be measured less accurately.

In addition, the opened shut-off unit 7 does not hinder the process of inserting an intracorporeal device, e.g., a catheter or an endoscope or another device at the port unit 28 into the device-side breathing air tube 21 and of passing it through the valve arrangement 1 into the patient-side breathing air tube 18 to the patient P.

As can be seen in the figures, the shut-off unit 7 is moved to and fro by a rotary movement by 90° between the closed position and the open position. These are the two end positions, into which the shut-off unit 7 according to the exemplary embodiment can be brought. The locking unit 10 is capable of locking the shut-off unit 7 in these two end positions. In one alternative, not shown, the locking unit 10 is capable of locking the actuating unit 12 additionally in an intermediate position and hence to lock the shut-off unit 7 additionally in an intermediate position. An angle between 0° and 90°, preferably between 300 and 600 and especially preferably an angle of 45° can occur between the longitudinal axis of the actuating unit 12 and the longitudinal axis of the fluid carrying unit 6 in this intermediate position.

The flow of fluid through the fluid carrying unit 6 is possible in this intermediate position as well. In one configuration, a pressure at the patient-side port 3, which is above the pressure limit, causes the shut-off unit 7 to be moved from the closed position into the intermediate position or into the open position shown in FIG. 12, depending on how high the pressure is. Since the shut-off unit 7 is also locked in the intermediate position, it is prevented from being unintentionally moved again into the closed position.

The shut-off unit 7 acts both as a safety element 13 and as an actuating element for the locking unit 10 at the same time. As long as the locking unit 10 is in a locked state, the actuating unit 12 can only be moved against the locking effect, in this case against a strong spring force. By a user actuating the safety element 13, the user moves the locking unit 10 into a released state, not shown. The spring 9 exerts a weaker force in this released state, and the actuating unit 12 can be rotated by 90°. This configuration reduces especially the risk that the shut-off unit 7 will be unintentionally moved into the closed position, and it reduces the force necessary to move the actuating unit 12.

While specific embodiments of the invention have been shown and described in detail to illustrate the application of the principles of the invention, it will be understood that the invention may be embodied otherwise without departing from such principles.

LIST OF REFERENCE CHARACTERS

1 Valve arrangement; it comprises the shut-off unit 7, the actuating unit 12, the locking unit 10, the pressure relief mechanism 8 and the two ports 3 and 4

2 Ventilation system; it comprises the ventilator 17, the valve arrangement 1, the breathing air tubes 21 and 18 as well as the breathing air filter 20

3 Patient-side port of the valve arrangement 1; connected to the patient-side breathing air tube 18

4 Device-side port of the valve arrangement 1; detachably connected to the device-side breathing air tube 21

5 Valve; it comprises the shut-off unit 7 and the actuating unit 12

6 Tubular fluid carrying unit of the valve arrangement 1; it connects the ports 3 and 4 to one another

7 Shut-off unit; it is capable of closing the fluid carrying unit 6 in a closed position

8 Pressure relief mechanism; it moves the shut-off unit 7 into the open position when the pressure at the patient-side port 3 is above the pressure limit

9 Spring of the locking unit 10

10 Locking unit; it comprises the spring 9 and the connection element 25; it holds the shut-off unit 7 in the open position in an open locked state

11 Adjusting unit; it makes it possible to change the pressure limit of the locking unit 10 or of the pressure relief mechanism 8

12 Actuating unit to actuate the locking unit 10; it can be moved between an open position and a closed position; connected to the spring 9 via the connection element 25

13 Safety element; it holds the locking unit 10 in the open locked state in an inoperative position, operates as the actuating element

14 Adjusting member in the form of a compression spring; it is capable of moving the locking unit 10 into the released state or into the open locked state

15 Pressure sensor; it measures the pressure that is present at the patient-side port 3 with the shut-off unit 7 closed

16 Transmitting unit; it transmits a measured value of the pressure sensor 15 to the receiving unit 19

17 Ventilator; connected to the valve arrangement 1 via the breathing air tube 21

18 Patient-side breathing air tube, connected to the patient-side port 3

19 Receiving device at the ventilator 17

20 Breathing air filter between the breathing air tube 21 and the ventilator 17

21 Device-side breathing air tube; detachably connected to the device-side port 4

22 Pressure relief valve in the device-side port 4

23 Locking body, which holds the compression spring 14 in a tensioned position in the locked position, connected by the nonreturn valve 24

24 Nonreturn valve, which is capable of moving the locking body 23 from the locked position into the released position

25 Mechanical connection element between the spring 9 and the actuating unit 12

26 Part of the patient-side coupling unit, arranged in the body of the patient P

27 Mouthpiece, connected to part 26; it belongs to the patient-side coupling unit

28 Port unit for a catheter or for an endoscope; arranged in the device-side breathing air tube 21

29 Filter for viruses and bacteria; arranged in the device-side breathing air tube 21

30 Adjusting member for rotating the actuating unit 12 about the axis of rotation DA

31 Control device, which receives signals from the non-return valve and actuates the adjusting member 30

DA Axis of rotation of the actuating unit 12

F Flow direction, in which breathing air flows from the patient P through the valve arrangement 1 to the ventilator 17

LA Longitudinal axis of the actuating unit 12

P Patient, connected to the patient-side breathing air tube 18, ventilated mechanically by the ventilator 17

What is claimed is:

1. A valve arrangement for a fluid carrying system, which establishes or is capable of establishing a fluid connection between a patient-side coupling unit and a ventilator, the valve arrangement comprising:
- a patient-side port;
- a device-side port;
- a shut-off unit moveable between an open position and a closed position, wherein the shut-off unit is configured to establish a fluid communication between the patient-side port and the device-side port with the shut-off unit being in the open position and wherein the fluid communication is at least partially interrupted with the shut-off unit being in the closed position; and
- a locking unit configured to lock in an open locked state the shut-off unit in the open position and to lock in a closed locked state the shut-off unit in the closed position, wherein the valve arrangement is configured, with the shut-off unit in the closed position and with a pressure above a preset pressure limit present at the patient-side port, to automatically move the shut-off unit against a locking effect of the locking unit into the open position.

2. A valve arrangement in accordance with claim 1, wherein the valve arrangement is configured such that an automatic movement of the shut-off unit into the open position based on the pressure present above the pressure limit causes the locking unit to be moved into the open locked state and to lock the shut-off unit in the open position.

3. A valve arrangement in accordance with claim 1, wherein the configuration of the valve arrangement to automatically move the shut-off unit against the locking effect of the locking unit into the open position with the pressure above the preset pressure limit present at the patient-side port comprises a pressure relief mechanism configured, with the shut-off unit in the closed position, to automatically move the shut-off unit against the locking effect of the locking unit into the open position with the pressure above the preset pressure limit at the patient-side port.

4. A valve arrangement in accordance with claim 3, further comprising an actuating unit mechanically connected to the shut-off unit, the actuating unit being configured to move the shut-off unit between the open position and the closed position and between the closed position and the open position, wherein the pressure relief mechanism is mechanically connected to the actuating unit and is configured, with the shut-off unit in the closed position and with a pressure above a preset pressure barrier limit at the patient-side port, to move the actuating unit against the locking effect of the locking unit such that the effected movement of the actuating unit moves the shut-off unit into the open position.

5. A valve arrangement in accordance with claim 3, wherein:
- the pressure relief mechanism comprises a triggering component and an adjusting member;
- the adjusting member is activable and is configured to move the shut-off unit against the locking effect of the locking unit into the open position; and
- the triggering component is configured to activate the adjusting member with the shut-off unit in the closed position and with a pressure above the preset pressure limit at the patient-side port.

6. A valve arrangement in accordance with claim 1, further comprising an actuating unit connected to the shut-off unit and being moveable between an open position, which corresponds to the open position of the shut-off unit, and a closed position, which corresponds to the closed position of the shut-off unit, wherein:
- a movement of the actuating unit from one position into the other position brings about a movement of the shut-off unit into the respective corresponding position; and
- a movement of the shut-off unit from the closed position into the open position brings about a movement of the actuating unit into the open position.

7. A valve arrangement in accordance with claim 1, further comprising a manually actuatable safety element, wherein:
- when in an inoperative position, the manually actuatable safety element holds the locking unit in the open locked state;
- the locking unit comprises a released state;
- the locking unit allows for movement of the shut-off unit in the released state; and
- an actuation of the safety element causes the locking unit to be moved into the released state.

8. A valve arrangement in accordance with claim 1, wherein the valve arrangement is configured to generate an alarm and to output the generated alarm or to transmit the generated alarm to a receiver located at a spatial distance, the alarm is generated in response to the shut-off unit being moved automatically into the open position on the basis of the pressure present above the pressure limit.

9. A valve arrangement in accordance with claim 1, further comprising a pressure sensor configured to measure pressure present at the patient-side port at least when the shut-off unit is in the closed position.

10. A valve arrangement in accordance with claim 9, further comprising:
- a transmitting unit; and
- a receiver located at a distance in space from the transmitting unit, wherein the transmitting unit is configured to receive a measured value from the pressure sensor and to transmit the received measured value to the receiver.

11. A valve arrangement in accordance with claim 1, wherein:
- the device-side port is detachably connected to a fluid carrying unit;
- the shut-off unit is mechanically coupled to the device-side port such that a movement of the shut-off unit into the closed position causes the fluid carrying unit to be separated from the device-side port.

12. A valve arrangement according to claim 1, in combination with a fluid carrying unit wherein the valve arrangement is in a fluid connection with the fluid carrying unit and the device-side port of the valve arrangement is detachably connected to the fluid carrying unit.

13. A valve arrangement in accordance with claim 1, wherein the locking unit is configured to apply a force to the shut-off unit to move the shut-off unit to the closed position in the closed locked state, wherein the shut-off unit is locked in the open position and the closed position exclusively via the locking unit.

14. A ventilation system comprising:
- a ventilator;
- a fluid carrying arrangement; and
- a valve arrangement, the valve arrangement comprising:
  - a patient-side port connected to the fluid carrying arrangement;
  - a device-side port connected by a portion of the fluid carrying arrangement to the ventilator;
  - a shut-off unit moveable between an open position and a closed position, wherein the shut-off unit is configured to establish a fluid communication between the patient-side port and the device-side port with the shut-off unit being in the open position and the fluid communication is at least partially interrupted with the shut-off unit being in the closed position; and
- a locking unit configured to lock in an open locked state the shut-off unit in the open position and to lock in a closed locked state the shut-off unit in the closed position, wherein the valve arrangement is configured, with the shut-off unit in the closed position and with a pressure above a preset pressure limit present at the patient-side port, to automatically move the shut-off unit against a locking effect of the locking unit into the open position.

15. A ventilation systemin accordance with claim 14, wherein the configuration of the valve arrangement to automatically move the shut-off unit against the locking effect of the locking unit into the open position with the pressure above the preset pressure limit present at the patient-side port comprises a pressure relief mechanism configured, with the shut-off unit in the closed position, to automatically move the shut-off unit against the locking effect of the locking unit into the open position with the pressure above the preset pressure limit at the patient-side port.

16. A ventilation system in accordance with claim 15, further comprising:
- an actuating unit mechanically connected to the shut-off unit, the actuating unit being configured to move the shut-off unit between the open position and the closed position and between the closed position and the open position, wherein the pressure relief mechanism is mechanically connected to the actuating unit and is configured, with the shut-off unit in the closed position and with a pressure above a preset pressure limit at the patient-side port, to move the actuating unit against the locking effect of the locking unit such that the effected movement of the actuating unit moves the shut-off unit into the open position.

17. A ventilation system in accordance with claim 15, wherein:
- the pressure relief mechanism comprises a triggering component and an adjusting member;
- the adjusting member is activable and the activated adjusting member is configured to move the shut-off unit against the locking effect of the locking unit into the open position; and
- the triggering component is configured to activate the adjusting member with the shut-off unit in the closed position and with a pressure above the preset pressure limit at the patient-side port.

18. A process for operating a ventilation system, wherein the ventilation system comprises a ventilator for ventilating a patient and a valve arrangement, wherein the valve arrangement comprises: a shut-off unit; a locking unit; a patient-side port; and a device-side port, wherein the shut-off unit is moveable between an open position and a closed position, a fluid connection is or may be established between the ventilator and the device-side port and a fluid connection is or may be established between a patient-side coupling unit and the patient-side port, the process comprising the steps of:
- ventilating a patient mechanically with the ventilator and with the two established fluid connections, wherein with the shut-off unit being in the open position, a fluid stream flows through the valve arrangement and the locking unit locks the shut-off unit in the open position during the mechanical ventilation;
- subsequently ending or interrupting the mechanical ventilation with the ventilator;
- moving the shut-off unit into the closed position; and
- locking, with the locking unit, the shut-off unit in the closed position; and
- with the shut-off unit in the closed position and upon a pressure at the patient-side port being above a preset pressure limit, moving the shut-off unit automatically into the open position against a locking effect of the locking unit.

19. A process in accordance with claim 18, wherein the step that the shut-off unit is moved into the open position causes the locking unit to lock the shut-off unit in the open position.

20. A process in accordance with claim 18, wherein the valve arrangement additionally comprises a pressure relief mechanism wherein the step that the shut-off unit is moved automatically against the locking effect into the open position is performed by the pressure relief mechanism.

* * * * *